United States Patent
Dinkar et al.

(10) Patent No.: US 9,394,443 B2
(45) Date of Patent: Jul. 19, 2016

(54) MOISTURE CURABLE ORGANOPOLYSILOXANE COMPOSITION

(71) Applicants: Sumi Dinkar, Bangalore (IN); Mihirkumar Patel Maheshbai, Bangalore (IN); Anantharaman Dhanabalan, Bangalore (IN)

(72) Inventors: Sumi Dinkar, Bangalore (IN); Mihirkumar Patel Maheshbai, Bangalore (IN); Anantharaman Dhanabalan, Bangalore (IN)

(73) Assignee: Momentive Performance Materials, Inc., Waterford, NY (US)

(*) Notice: Subject to any disclaimer, the term of this patent is extended or adjusted under 35 U.S.C. 154(b) by 0 days.

(21) Appl. No.: 14/357,346

(22) PCT Filed: Nov. 9, 2012

(86) PCT No.: PCT/US2012/064411
§ 371 (c)(1),
(2) Date: May 9, 2014

(87) PCT Pub. No.: WO2013/071078
PCT Pub. Date: May 16, 2013

(65) Prior Publication Data
US 2014/0343202 A1 Nov. 20, 2014

Related U.S. Application Data

(60) Provisional application No. 61/558,133, filed on Nov. 10, 2011.

(51) Int. Cl.

| | | |
|---|---|---|
| C08L 83/04 | (2006.01) |
| B01J 31/22 | (2006.01) |
| C08G 77/08 | (2006.01) |
| C07F 15/02 | (2006.01) |
| C08K 5/12 | (2006.01) |
| C08K 5/42 | (2006.01) |
| C08K 5/52 | (2006.01) |
| C09D 183/04 | (2006.01) |
| C09J 183/04 | (2006.01) |
| C08G 77/16 | (2006.01) |

(52) U.S. Cl.
CPC .......... *C08L 83/04* (2013.01); *B01J 31/2234* (2013.01); *C07F 15/02* (2013.01); *C08G 77/08* (2013.01); *C08K 5/12* (2013.01); *C08K 5/42* (2013.01); *C08K 5/52* (2013.01); *C09D 183/04* (2013.01); *C09J 183/04* (2013.01); *B01J 2231/14* (2013.01); *B01J 2531/54* (2013.01); *B01J 2531/842* (2013.01); *C08G 77/16* (2013.01)

(58) Field of Classification Search
CPC ........................................................ C08L 83/04
USPC ........................................................ 524/141
See application file for complete search history.

(56) References Cited

U.S. PATENT DOCUMENTS

| | | |
|---|---|---|
| 2,191,587 A | 2/1940 | Rethreck |
| 2,958,688 A | 11/1960 | Brooks et al. |
| 3,278,457 A | 10/1966 | Milgrom |
| 3,278,458 A | 10/1966 | Melner |
| 3,278,459 A | 10/1966 | Johnston |
| 3,427,256 A | 2/1969 | Milgrom |
| 3,427,334 A | 2/1969 | Belner |
| 3,427,335 A | 2/1969 | Herold |
| 3,627,722 A | 12/1971 | Seiter |
| 3,632,557 A | 1/1972 | Brode |
| 3,786,081 A | 1/1974 | Bishop |
| 3,890,269 A | 6/1975 | Martin |
| 3,936,578 A | 2/1976 | Dumoulin et al. |
| 3,960,575 A | 6/1976 | Martin |
| 3,971,751 A | 7/1976 | Isayama et al. |
| 4,247,330 A | 1/1981 | Sanders, Jr. |
| 4,248,992 A | 2/1981 | Takago |
| 4,293,597 A | 10/1981 | Bessmer et al. |
| 4,312,801 A | 1/1982 | Hiriart Bodin et al. |
| 4,345,053 A | 8/1982 | Rizk et al. |
| 4,379,766 A | 4/1983 | Mack et al. |
| 4,404,348 A | 9/1983 | Fau et al. |
| 4,410,677 A | 10/1983 | Lampe |
| 4,461,867 A | 7/1984 | Surprenant |
| 4,481,367 A | 11/1984 | Knopf |
| 4,528,353 A | 7/1985 | Lucas et al. |

(Continued)

FOREIGN PATENT DOCUMENTS

| | | |
|---|---|---|
| EP | 543292 A1 | 5/1993 |
| EP | 0604997 A2 | 7/1994 |

(Continued)

OTHER PUBLICATIONS

International Search Report and Written Opinion of the International Searching Authority dated Oct. 17, 2012 for PCT/US2011/060156.

(Continued)

*Primary Examiner* — Doris Lee

(74) *Attorney, Agent, or Firm* — McDonald Hopkins LLC

(57) ABSTRACT

The present invention provides curable compositions comprising non-Sn organo-metal catalysts that accelerate the condensation curing of moisture curable silicones/non-silicones. In particular, the present invention provides Fe(III) and Bi(III) complexes that are particularly suitable as replacements for organotin for sealant and RTV formulations. The Fe(III) and Bi(III) complexes are comparable or superior to organotin such as DBTDL and exhibit certain behavior in the presence of components that allow for tuning or adjusting the cure characteristics of the present compositions and provide good adhesion and storage stability.

28 Claims, No Drawings

(56) References Cited

U.S. PATENT DOCUMENTS

| | | |
|---|---|---|
| 4,537,942 A | 8/1985 | Brown-Wensley et al. |
| 4,612,054 A | 9/1986 | Hamon |
| 4,625,012 A | 11/1986 | Rizk et al. |
| 4,665,116 A | 5/1987 | Kornhaber et al. |
| 4,769,412 A | 9/1988 | Inoue et al. |
| 4,985,491 A | 1/1991 | Reisch |
| 5,194,489 A | 3/1993 | Frances et al. |
| 5,304,621 A | 4/1994 | Staiger et al. |
| 5,395,860 A | 3/1995 | Leung et al. |
| 5,472,987 A | 12/1995 | Reedy et al. |
| 5,502,144 A | 3/1996 | Kuo et al. |
| 5,623,044 A | 4/1997 | Chiao |
| 5,741,839 A | 4/1998 | Scheim |
| 5,840,428 A | 11/1998 | Blizzard et al. |
| 5,852,137 A | 12/1998 | Hsieh et al. |
| 5,858,280 A | 1/1999 | Zhang et al. |
| 5,919,888 A | 7/1999 | Lawrey et al. |
| 5,932,650 A | 8/1999 | Bayly |
| 5,945,466 A | 8/1999 | Ikeno et al. |
| 5,985,991 A | 11/1999 | Beljanski et al. |
| 6,072,013 A | 6/2000 | Manzouji et al. |
| 6,162,756 A | 12/2000 | Friebe et al. |
| 6,197,912 B1 | 3/2001 | Huang et al. |
| 6,207,794 B1 | 3/2001 | Yamasaki et al. |
| 6,303,731 B1 | 10/2001 | Carlson et al. |
| 6,310,170 B1 | 10/2001 | Johnston et al. |
| 6,359,101 B1 | 3/2002 | O'Connor et al. |
| 6,369,184 B1 | 4/2002 | Bohin et al. |
| 6,515,164 B1 | 2/2003 | Bolte et al. |
| 6,599,633 B1 | 7/2003 | Wolf et al. |
| 6,696,383 B1 | 2/2004 | Le-Khac et al. |
| 6,753,400 B2 | 6/2004 | Inoue et al. |
| 6,827,875 B2 | 12/2004 | Schelhaas et al. |
| 6,833,423 B2 | 12/2004 | Roesler et al. |
| 6,875,864 B2 | 4/2005 | Pillai et al. |
| 6,911,109 B2 | 6/2005 | Giroux et al. |
| 6,919,293 B1 | 7/2005 | Ooms et al. |
| 7,115,695 B2 | 10/2006 | Okamoto et al. |
| 7,351,782 B2 | 4/2008 | Wakabayashi et al. |
| 7,365,145 B2 | 4/2008 | Yang et al. |
| 7,504,468 B2 | 3/2009 | Guennouni et al. |
| 7,527,838 B2 | 5/2009 | Correia |
| 7,550,547 B2 | 6/2009 | Wakabayashi et al. |
| 7,553,901 B2 | 6/2009 | Horikoshi et al. |
| 7,569,653 B2 | 8/2009 | Landon |
| 7,605,220 B2 | 10/2009 | Wakabayashi et al. |
| 7,642,331 B2 | 1/2010 | Pouchelon et al. |
| 7,732,554 B2 | 6/2010 | O'Keefe et al. |
| 7,772,332 B2 | 8/2010 | Wakabayashi et al. |
| 7,781,513 B2 | 8/2010 | Lucas et al. |
| 7,863,398 B2 | 1/2011 | Devi et al. |
| 8,076,401 B2 | 12/2011 | Schindler et al. |
| 8,242,226 B2 | 8/2012 | Maliverney et al. |
| 8,426,546 B2 | 4/2013 | Maliverney et al. |
| 8,461,283 B2 | 6/2013 | Maliverney et al. |
| 8,586,688 B2 | 11/2013 | Okamoto et al. |
| 2002/0146573 A1 | 10/2002 | Shimada et al. |
| 2002/0156210 A1 | 10/2002 | Luo |
| 2002/0198352 A1 | 12/2002 | Tanaka |
| 2003/0069379 A1 | 4/2003 | Inoue et al. |
| 2004/0122253 A1 | 6/2004 | Smith |
| 2004/0127669 A1 | 7/2004 | Ueno et al. |
| 2005/0020706 A1 | 1/2005 | Kollbach |
| 2005/0054765 A1 | 3/2005 | Putzer |
| 2005/0137322 A1 | 6/2005 | Roesler |
| 2005/0171315 A1 | 8/2005 | Wakabayashi et al. |
| 2006/0019398 A1 | 1/2006 | Corson et al. |
| 2007/0060732 A1* | 3/2007 | Yang et al. ................. 528/44 |
| 2007/0191541 A1 | 8/2007 | Guennouni et al. |
| 2007/0197820 A1 | 8/2007 | Van Holen et al. |
| 2007/0203297 A1 | 8/2007 | Wakabayashi et al. |
| 2007/0237912 A1 | 10/2007 | Correia |
| 2007/0275255 A1 | 11/2007 | Ooms |
| 2008/0039565 A1 | 2/2008 | Ridley et al. |
| 2008/0076843 A1 | 3/2008 | Clark |
| 2008/0188624 A1 | 8/2008 | Yano |
| 2009/0018260 A1 | 1/2009 | Correia et al. |
| 2009/0082553 A1* | 3/2009 | Satake et al. ................. 534/595 |
| 2009/0087635 A1 | 4/2009 | Yano |
| 2009/0088547 A1 | 4/2009 | Schamschurin et al. |
| 2009/0156737 A1 | 6/2009 | Schindler |
| 2009/0182091 A1 | 7/2009 | Noro |
| 2009/0182099 A1 | 7/2009 | Noro et al. |
| 2009/0186993 A1 | 7/2009 | Noro et al. |
| 2009/0215944 A1* | 8/2009 | Maton et al. ................. 524/413 |
| 2009/0299017 A1 | 12/2009 | Tsuno et al. |
| 2009/0306307 A1 | 12/2009 | Ahn et al. |
| 2010/0063215 A1 | 3/2010 | Yano et al. |
| 2010/0152373 A1 | 6/2010 | Wakabayashi et al. |
| 2010/0184883 A1 | 7/2010 | Detemmerman et al. |
| 2010/0197855 A1 | 8/2010 | Blom et al. |
| 2010/0234510 A1 | 9/2010 | Feder |
| 2011/0009558 A1 | 1/2011 | Maliverney |
| 2011/0021684 A1 | 1/2011 | Maliverney |
| 2011/0028640 A1 | 2/2011 | Klein et al. |
| 2011/0028647 A1 | 2/2011 | Sixt et al. |
| 2011/0040034 A1 | 2/2011 | Maliverney |
| 2011/0043034 A1 | 2/2011 | Pien |
| 2011/0046299 A1 | 2/2011 | Maliverney et al. |
| 2011/0098392 A1 | 4/2011 | Barrandon et al. |
| 2011/0098420 A1 | 4/2011 | Takizawa |
| 2011/0124802 A1 | 5/2011 | Maliverney et al. |
| 2011/0281969 A1 | 11/2011 | Maliverney |
| 2012/0016063 A1 | 1/2012 | Maton et al. |
| 2012/0065308 A1 | 3/2012 | Sumi |
| 2012/0172471 A1 | 7/2012 | Maliverney |
| 2012/0172473 A1 | 7/2012 | Maliverney |

FOREIGN PATENT DOCUMENTS

| | | |
|---|---|---|
| EP | 625548 A2 | 11/1994 |
| EP | 0947531 B1 | 7/2001 |
| EP | 1230298 B1 | 9/2003 |
| EP | 1731573 A1 | 12/2006 |
| EP | 2130873 A1 | 12/2009 |
| EP | 1985666 B1 | 12/2010 |
| EP | 1550700 B1 | 1/2011 |
| EP | 2388297 A1 | 11/2011 |
| EP | 2246393 A1 | 6/2014 |
| JP | 63245466 A | 10/1988 |
| JP | 63565924 A | 11/1988 |
| JP | 5039428 A | 2/1993 |
| JP | 5117518 A | 5/1993 |
| JP | 6049210 A | 2/1994 |
| JP | 6073291 A | 3/1994 |
| JP | 6212077 A | 8/1994 |
| JP | 8041358 A | 8/1994 |
| JP | 635973 A | 12/1994 |
| JP | 7179762 A | 7/1995 |
| JP | 625548 B1 | 1/1998 |
| JP | 10101932 A | 4/1998 |
| JP | 11029713 A | 2/1999 |
| JP | 2001089618 A | 4/2001 |
| JP | 20123342363 | 12/2001 |
| JP | 2003119387 A | 4/2003 |
| JP | 20066225629 | 8/2006 |
| JP | 2006316287 A | 11/2006 |
| JP | 2008231142 A | 10/2008 |
| JP | 20100013524 A | 1/2010 |
| JP | 04472632 B2 | 6/2010 |
| JP | 2010168590 A | 8/2010 |
| JP | 04699897 B2 | 6/2011 |
| JP | 2011153309 A | 8/2011 |
| JP | 04814733 B2 | 11/2011 |
| JP | 04874650 B2 | 2/2012 |
| JP | 05080006 B2 | 11/2012 |
| WO | 0060010 A1 | 10/2000 |
| WO | 2007064621 A1 | 6/2007 |
| WO | 2009106719 A1 | 9/2009 |
| WO | 2009106722 A1 | 9/2009 |
| WO | 2012134788 A1 | 10/2012 |
| WO | 2013013111 A1 | 1/2013 |
| WO | 2013026654 A1 | 2/2013 |

(56) References Cited

FOREIGN PATENT DOCUMENTS

| WO | 2013070227 | A1 | 5/2013 |
|----|------------|----|--------|
| WO | 2013117471 | A1 | 5/2013 |
| WO | 2013142140 | A1 | 9/2013 |

OTHER PUBLICATIONS

International Search Report and Written Opinion of the International Searching Authority dated Jan. 22, 2013 and for PCT/US2012/06441.
Extended European Search Report of the European Searching Authority dated May 8, 2015 for EP 12847749.4.
Patel et al., "Impact of thermal ageing on the tin catalyst species in room temperature vulcanised polysiloxane rubbers", Polymer Degradation and Stability, 83 (2004) pp. 157-161.
Toynbee, "Silane crosslinking of polyolefins: observations on the tin catalyst employed", Polymer, vol. 35, No. 2, 1994.
Goddard et al., Principles of Polymer Science and Technology in Cosmetics and Personal Care, 1999, Chapter 7, Marcel Dekker, Inc., New York, New York.
US 5,536,414, 6/1996, Delfert et al. (withdrawn)
Pubchem Substance Summary for ST51001443 Create Date Sep. 18, 2005.
Pubchem Substance Summary for CHEMBL 1083796 Deposit Date Dec. 22, 2010; Modify Date Feb. 4, 2013.
Glasovac, Z et al. "Synthesis of Highly Basic Hexasubstituted Biguanides by Environmentally Friendly Methods" Synlett, Oct. 14, 2013, pp. 2540-2544.
Grzelka et al., "Polysilxanol condensation and disproportionation in the presence of a superacid", Journal of Organic Chemistry, vol. 689, Issue 4 (2004), 705-713.
Munirathinam, R. et al., "Gallium-containing polymer brush film as efficient supported Lewis acid catalyst in a glass microractor." Beilstein Journal of Organic Chemistry. vol. 9 2013. pp. 1698-1704.
First Office Action, CN 201280066735.3, dated Jun. 30, 2015.
First Office Action, JP 2015-541320, dated Apr. 21, 2015.
Second Office Action, JP 2015-541320, dated Oct. 27, 2015.

* cited by examiner

MOISTURE CURABLE ORGANOPOLYSILOXANE COMPOSITION

RELATED APPLICATIONS

This application is a 35 U.S.C. 371 national stage filing and claims priority to PCT Application No. PCT/US2012/064411, filed Nov. 9, 2012, which claims priority to and the benefit of U.S. Provisional Application 61/558,133 filed on Nov. 10, 2011 and titled "Moisture Curable Organopolysiloxane Composition," the disclosures of which are each incorporated herein by reference in their entirety.

FIELD

The present invention relates to curable compositions comprising curable polymers having reactive terminal silyl groups and iron-based or bismuth based catalysts. In particular, the present invention provides curable compositions comprising Fe(III)-based or Bi(III)-based complexes as alternatives to organotin catalysts.

BACKGROUND

Polymers having reactive terminal silyl groups or compositions comprising such polymers can be hydrolyzed and condensed in the presence of water and organometal catalysts. Suitable known catalysts for curable compositions include organometallic compounds employing metals such as Sn, Ti, Zn or Ca. Organotin compounds such as, for example, dibutyltin dilaurate (DBTDL) are widely used as condensation cure catalysts to accelerate the moisture assisted curing of a number of different polyorganosiloxanes and non-silicone polymers having reactive terminal silyl groups such as room temperature vulcanizing (RTV) formulations including RTV-1 and RTV-2 formulations. Environmental regulatory agencies and directives, however, have increased or are expected to increase restrictions on the use of organotin compounds in formulated products. For example, while formulations with greater than 0.5 wt. % dibutyltin presently require labeling as toxic with reproductive 1B classification, dibutyltin-containing formulations are proposed to be completely phased out in consumer applications during next 4-6 years.

Alternative organotin compounds such as dioctyltin compounds and dimethyltin compounds can only be considered as a short-term remedial plan, as these organotin compounds may also be regulated in the future. It would be beneficial to identify non-Sn metal catalysts that accelerate the condensation curing of moisture curable silicones and non-silicones. Desirably, substitutes for organotin catalysts should exhibit properties similar to organotin compounds in terms of curing, storage, and appearance. Non-tin catalysts would also desirably initiate the condensation reaction of the selected polymers and complete this reaction upon the surface and may be in the bulk in a desired time schedule. There are therefore many proposals for the replacement of organometallic tin compounds by other organometallic compounds. These other metals have specific advantages and disadvantages in view of replacing tin compounds perfectly. Therefore, there is still a need to overcome some of the weaknesses of possible metal compounds as suitable catalyst for condensation cure reaction and behavior of uncured and cured compositions in particular to maintain the ability to adhere onto the surface of several substrates.

The use of iron (III) and bismuth (III) complexes as catalysts in condensation curable silicone compositions has been described. For example, U.S. Pat. Nos. 7,550,547 and 7,115,695 describe the use of iron carboxylate as a catalyst for cross-linking silyl-capped organic polymers, with and without carboxylic acids, respectively. U.S. Pub. No. 2011/0021684 and 2011/0040034 describes the synthesis and use of iron complexes that contain both diketonate or enolate anions and monovalent anions as catalysts in RTV-organosiloxane compositions. U.S. Pat. Nos. 4,404,348 and 3,936,578 claim the use of iron acetylacetonates as catalyst in solventless organosiloxane coating/impregnating compositions. U.S. Pat. No. 5,932,650 describes the use of iron carboxylate to improve high temperature adhesion of RTV-1 silicone composition which comprises organometallic tin as condensation cure catalyst. U.S. Pat. No. 5,985,991 broadly claims the use of among others, e.g., iron acetylacetonate in a generic list of metal acetylacetonates consisting of Cu, Cr, Al, Zn, Ti and Zr to improve the oil resistance of RTV silicone composition which comprises metal salt of carboxylic acid as a condensation cure catalyst. U.S. Pat. No. 5,945,466 broadly claims among others, e.g. organic metal compounds containing Fe in a generic list of organic metal compounds containing Sn, Ti, Zr, Pd, Zn, Co, Mn and Al as metallic element, as curing catalyst for room temperature curable organopolysiloxane composition which contains organosilane or its hydrolyzed product among other components.

U.S. Publication Nos. 2003/0069379 claims the use of trivalent bismuth carboxylates as curing catalyst in room temperature curing organopolysiloxane composition. U.S. Publication No. 2011/0009558 and 2011/0021684 claims the use of Bi(monoallyl ethylene glycolate)$_3$ and Bi(1,1,1,5,5,5-hexafluoropentanedionate)$_3$ as catalysts, respectively, in curable organopolysiloxane compositions. U.S. Pat. No. 7,365,145 generically claims, among others, organo iron and organo bismuth compounds in a generic list of organic dibutyltin, zirconium complex, aluminum chelate, titanium chelate, organic zinc, organic cobalt, and organic nickel as catalysts in moisture curable silylated polymer composition. U.S. Pat. No. 5,194,489 claims the use of bismuth carboxylate as hardening catalyst for crosslinkable cyclopentenyl containing diorganopolysiloxane composition which also comprises an inorganic filler. U.S. Publication No. 2009/0156737 claims among others Lewis acid compounds of bismuth in a generic list of Lewis acid compounds of Ti, Zr, Hf, Zn, B, Al as catalysts in polymer blends comprising alkoxy silane terminated polymers and fillers. Similar generic descriptions on the use of bismuth carboxylate in curable silicone composition are made in U.S. Publication no. 2009/306307. U.S. Pat. No. 7,504,468 claims the use of mixture organometallic compounds which include among others bismuth compounds as catalyst in single component silicone compositions. U.S. Publication no. 2005/0137322 claims the use of a bismuth catalyst in a second component along with a polyol in two component coating composition comprised of a compound containing trialkoxysilyl and isocyanate functional groups as a first component.

U.S. Pat. No. 4,293,597 includes Fe and Bi salts of mono- or di-carboxylic acids in a generic list of metal salts including Pb, Sn, Zr, Sb, Cd, Ba, Ca, and Ti as catalysts in curable silicone rubber compositions that also contains nitrogen-functional silanes. U.S. Pat. No. 4,461,867 includes Fe and Bi metal esters in a generic list of metal esters also including Sn, Pb, Zr, Sb, Cd, Ba, Ca, Ti, Mn, Zn, Cr, Co, Ni, Al, Ga and Ge as a catalyst in moisture curable RTV-1 silicone compositions. U.S. Pub. No. 2011/0098420 includes, among others, Fe and Bi compounds in a generic list also including compounds of Pt, Pd, Pb, Sn, Zn, Ti and Zr, as dehydrogenative condensation reaction catalyst for a curable polysiloxane composition comprising of siloxanes with 2 or more hydrosilyl groups and siloxanes with 2 or more silanol groups. U.S. Pat. No. 7,527,838 claims, among others, Fe and Bi based catalysts in a generic list which includes other metal catalysts based on Sn, Ti, Zr, Pb, Co, Sb, Mn and Zn, in curable diorganopolysiloxane compositions used for making insulated glass units. U.S. Publication number 2002/0156210 claims the use of catalyst composition that is the combination of or the reaction products of ingredients comprising iron containing compounds that include, among others, iron carboxylates and iron acetylacetonates, silyl phosphates and organoaluminium compounds in the process of forming conjugated diene polymers.

Despite these general teachings that group iron or bismuth complexes together with other metal catalysts, there has not been provided any teachings or catalyst compositions that differentiate the catalytic activity exhibited by different iron or bismuth complexes. Further, there has not been a replacement catalyst for organo-tin compounds that maintains its ability to cure after storage over months in a sealed cartridge, when exposed to humidity or ambient air. It is always a specific requirement for moisture curable compositions to achieve the shortest possible curing times, showing a tack-free surface as well as a curing through the complete bulk in thick section for "One-Part" and "Two-Part" Room-Temperature Vulcanizing (RTV) compositions and provide a reasonable adhesion after cure onto a variety of substrates.

SUMMARY

The present invention provides tin-free, curable compositions comprising silyl-terminated polymers and a non-toxic condensation catalyst based on iron or bismuth complexes. In particular, the present invention provides curable compositions employing a Fe(III)-based complex or a Bi(III)-based as a condensation catalyst. In one aspect, the Fe(III)-based catalysts are complexes of the Formula (1):

$$Fe^{III}Y_{3-c}A_c \quad (1)$$

and the Bi(III)-based catalysts are complexes of the Formula (2):

$$Bi^{III}Y_{3-c}A_c \quad (2)$$

wherein Y is a chelating ligand, A is an anion, and c is a number between 0 to 2 or an integer.

In one aspect, the invention provides a curable composition exhibiting a relatively short tack-free time, curing through the bulk, as well as long storage stability in the cartridge, i.e., in the absence of humidity. The inventors have unexpectedly found that Fe(III) or Bi(III) compounds, including compounds of formulas (1) or (2), in combination with certain adhesion promoter components and acidic compounds exhibit curing behavior similar to or even better than organotin compounds, and are therefore suitable as replacements for organotin catalysts in compositions having a reactive, silyl-terminated polymer that can undergo condensation reactions such as in RTV-1 sealant and RTV-2 formulations.

Curable compositions using selected Fe(III) or Bi(III) compounds may also exhibit certain storage stability of the uncured composition in the cartridge, adhesion onto several surfaces, and a cure rate in a predictable time scheme.

In one aspect, the present invention provides a composition for forming a cured polymer composition comprising (A) a polymer having at least a reactive silylgroup; (B) a crosslinker or chain extender chosen from an alkoxysilane, an alkoxysiloxane, an oximosilane, an oximosiloxane, an enoxysilane, an enoxysiloxane, an aminosilane, a carboxysilane, a carboxysiloxane, an alkylamidosilane, an alkylamidosiloxane, an arylamidosilane, an arylamidosiloxane, an alkoxyaminosilane, an alkaryaminosiloxane, an alkoxycarbamatosilane, an alkoxycarbamatosiloxane, and combinations of two or more thereof; (C) about 0.01-7 parts per weight per 100 parts per weight of the polymer (A) of a catalyst selected from the group of organometallic compounds or salts of iron (III) (Fe-III) or bismuth (III) (Bi-III); (D) at least one adhesion promoter chosen from a silane or siloxane other than the compounds listed under (B); (E) optionally, a filler component; and (F) at least one acidic compound chosen from a phosphate ester, a phosphonate, a phosphite, a phosphine, a sulfite, a pseudohalogenide, a branched $C_4$-$C_{25}$-alkyl carboxylic acid, or a combination of two or more thereof.

According to one embodiment, Y is a chelating ligand chosen from a diketonate, a diamine, a triamine, an aminoacetate, a nitriloacetate, a bipyridin, a glyoxime, or a combination of two or more thereof; and A is an anion, and c is a number between 0 to 2 or an integer. According to one embodiment, the chelating agent Y comprises a substituted or unsubstituted diketonate. The anion A is selected from group which consists of substituted, unsubstituted $C_4$-$C_{25}$-alkyl-, $C_7$-$C_{25}$-arylalkyl, $C_7$-$C_{25}$-alkylaryl and $C_6$-$C_{10}$-aryl carboxylate anions. According to one embodiment, comprises octoate, 2-ethylhexanoate, decanoate, or a combination of two or more thereof.

According to one embodiment, the anion A is chosen from a branched $C_4$-$C_{19}$-alkyl carboxylic acid.

According to one embodiment, the component (F) is chosen from a mono ester of a phosphate; a phosphonate of the formula $(R^3O)PO(OH)_2$, $(R^3O)P(OH)_2$, or $R^3P(O)(OH)_2$ where $R^3$ is a $C_1$-$C_{18}$-alkyl, a $C_2$-$C_{20}$-alkoxyalkyl, phenyl, a $C_7$-$C_{12}$-alkylaryl, a poly($C_2$-$C_4$-alkylene) oxide ester or its mixtures with diesters; a branched alkyl $C_4$-$C_{14}$-alkyl carboxylic acid; or a combination of two or more thereof.

In another aspect, the polymer (A) has the formula: $[R^1_aR^2_{3-a}Si-Z-]_n-X-Z-SiR^1_aR^2_{3-a}$. In another embodiment, X is chosen from a polyurethane; a polyester; a polyether; a polycarbonate; a polyolefin; a polypropylene; a polyesterether; and a polyorganosiloxane having units of $R_3SiO_{1/2}$, $R_2SiO$, $RSiO_{3/2}$, and/or $SiO_{4/2}$, n is 0 to 100, a is 0 to 2, R and $R^1$ can be identical or different at the same Si-atom and chosen from a $C_1$-$C_{10}$-alkyl; a $C_1$-$C_{10}$-alkyl substituted with one or more of Cl, F, N, O or S; a phenyl; a $C_7$-$C_{16}$-alkylaryl; a $C_7$-$C_{16}$-arylalkyl; a $C_2$-$C_4$-polyalkylene ether; or a combination of two or more thereof. In yet another aspect, $R^2$ is chosen from OH, a $C_1$-$C_8$-alkoxy, a $C_2$-$C_{18}$-alkoxyalkyl, an oximoalkyl, an enoxyalkyl, an aminoalkyl, a carboxyalkyl, an amidoalkyl, an amidoaryl, a carbamatoalkyl, or a combination of two or more thereof, and Z is a bond, a divalent unit selected from the group of a $C_1$-$C_8$-alkylene, or O.

According to one embodiment, the crosslinker component (B) is chosen from tetraethylorthosilicate (TEOS), a polycondensate of TEOS, methyltrimethoxysilane (MTMS), vinyltrimethoxysilane, methylvinyldimethoxysilane, dimethyldiethoxysilane, vinyltriethoxysilane, tetra-n-propylorthosilicate, vinyltris(methylethylketoxime)silane, methyltris(methylethylketoxime)silane, trisacetamidomethylsilane, bisacetamidodimethylsilane, tris(N-methyl-acetamido)methylsilane, bis(N-methylacetamido)dimethylsilane, (N-methyl-acetamido)methyldialkoxysilane, trisbenzamidomethylsilane, trispropenoxymethylsilane, alkyldialkoxyamidosilanes, alkylalkoxybisamidosilanes, $CH_3Si(OC_2H_5)_{1-2}(NHCOR)_{2-1}$, $(CH_3Si(OC_2H_5)(NCH_3COC_6H_5)_2$, $CH_3Si(OC_2H_5)-(NHCOC_6H_5)_2$, methyldimethoxy(ethylmethylketoximo)silane; methylmethoxybis-(ethylmethylketoximo)silane; methyldimethoxy(acetal-doximo)silane; methyldimethoxy(N-methylcarbamato)silane; ethyldimethoxy(N-methyl-carbamato)silane; methyldimethoxyisopropenoxysilane; trimethoxyisopropenoxysilane; methyltri-iso-propenoxysilane; methyldimethoxy(but-2-ene-2-oxy)silane; methyldimethoxy(1-phenylethenoxy)silane; methyldimethoxy-2(1-carboethoxypropenoxy)silane; methylmethoxydi-N-methylaminosilane; vinyldimethoxymethylaminosilane; tetra-N,N-diethylaminosilane; methyldimethoxymethylaminosilane; methyltricyclohexylaminosilane; methyldimethoxy-ethylaminosilane; dimethyl di-N,N-dimethylaminosilane; methyldimethoxyisopropylaminosilane dimethyldi-N,N-diethylaminosilane; ethyldimethoxy(N-ethylpropionamido)silane; methyldi-methoxy(N-methylacetamido)silane; methyltris(N-methylacetamido)silane; ethyldimethoxy(N-methylacetamido)silane; methyltris(N-methylbenzamido)silane; methylmethoxybis(N-methylacetamido)silane; methyldimethoxy(caprolactamo)silane; trimethoxy(N-methylacetamido)silane; methyl dimethoxyethylacetimidatosilane; methyldimethoxy-propylacetimidatosilane; methyl dimethoxy(N,N',N'-trimethylureido)silane; methyldimethoxy(N-allyl-N',N'-dimethylureido) silane; methyldimethoxy(N-phenyl-N',N'-dimethylureido) silane; methyldimethoxyisocyanatosilane; dimethoxydiisocyanatosilane; methyldimethoxythioisocyanatosilane; methylmethoxydithioisocyanatosilane, or a combination of two or more thereof.

According to one embodiment, the adhesion promoter component (D) is chosen from an aminoalkyltrialkoxysilane, an aminoalkylalkyldialkoxysilane, a bis(alkyltrialkoxysilyl) amine, a tris(alkyltrialkoxysilyl)amine, a tris(alkyltrialkoxysilyl)cyanuarate, and a tris(alkyltrialkoxy-silyl)isocyanurate, or a combination of two or more thereof.

According to one embodiment, the composition comprises about 1 to about 10 wt. % of the crosslinker component (B) based on 100 wt. % of the polymer component (A).

According to one embodiment, the crosslinker component (B) is chosen from a silane or a siloxane, the silane or siloxane having two or more reactive groups that can undergo hydrolysis and/or condensation reaction with polymer (A) or on its own in the presence of water and component (F).

According to one embodiment, the polymer component (A) is chosen from a polyorganosiloxane comprising divalent units of the formula [$R_2SiO$] in the backbone, wherein R is chosen from a $C_1$-$C_{10}$-alkyl; a $C_1$-$C_{10}$ alkyl substituted with one or more of Cl, F, N, O or S; a phenyl; a $C_7$-$C_{16}$ alkylaryl; a $C_7$-$C_{16}$ arylalkyl; a $C_2$-$C_4$ polyalkylene ether; or a combination of two or more thereof.

According to one embodiment, the catalyst (C) is present in an amount of from about 0.2 to about 0.7 wt. pt. per 100 wt. pt. of component (A).

According to one embodiment, the component (F) is present in an amount of from about 0.02 to about 3 wt. pt. per 100 wt. pt. of component (A).

According to one embodiment, the polymer component (A) has the formula: $R^2_{3-a}R^1_aSi$—Z—[$R_2SiO$]$_x$[$R^1_2SiO$]$_y$—Z—$SiR^1_aR^2_{3-a}$ whereby x is 0 to 10000; y is 0 to 1000; a is 0 to 2; R is methyl. In another aspect, R' is chosen from a $C_1$-$C_{10}$-alkyl; a $C_1$-$C_{10}$ alkyl substituted with one or more of Cl, F, N, O or S; a phenyl; a $C_7$-$C_{16}$ alkylaryl; a $C_7$-$C_{16}$ arylalkyl; a $C_2$-$C_4$ polyalkylene ether; or a combination of two or more thereof, and other siloxane units may be present in amounts less than 10 mol. % preferably methyl, vinyl, phenyl. In yet another embodiment, $R^2$ is chosen from OH, a $C_1$-$C_8$-alkoxy, a $C_2$-$C_{18}$-alkoxyalkyl, an oximoalkyl, an enoxyalkyl, an aminoalkyl, a carboxyalkyl, an amidoalkyl, an amidoaryl, a carbamatoalkyl, or a combination of two or more thereof, and Z is —O—, bond, or —$C_2H_4$—.

According to one embodiment, the composition further comprises a solvent chosen from an alkylbenzene, a trialkyphosphophate, a triarylphosphate, a phthalic acid ester, an arylsulfonic acid ester having a viscosity-density constant (VDC) of at least 0.86 that is miscible with a polyorganosiloxanes and catalyst component (C), a polyorganosiloxane devoid of reactive groups and having a viscosity of less than 2000 mPa·s at 25° C., or a combination of two or more thereof.

According to one embodiment, the composition is provided as a one part composition.

According to one embodiment, the composition comprises 100 pt. wt of component (A), 0.1 to about 10 pt. wt. of at least one crosslinker (B), 0.01 to about 7 pt. wt. of a catalyst (C), 0.1 to about 5 pt. wt. of an adhesion promoter (D), 0 to about 300 pt. wt. of component (E), 0.01 to about 8 pt. wt. of component (F) whereby this composition can be stored in the absence of humidity and is curable in the presence of humidity upon exposure to ambient air.

According to one embodiment, the composition is a two-part composition comprising: (i) a first portion comprising the polymer component (A), optionally the filler component (E), and optionally the acidic compound (F); and (ii) a second portion comprising the crosslinker (B), the catalyst component (C), the adhesive promoter (D), and the acidic compound (F), whereby (i) and (ii) are stored separately until applied for curing by mixing of the components (i) and (ii).

According to one embodiment, portion (i) comprises 100% wt. of component (A), and 0 to 70 pt. wt. of component (E); and portion (ii) comprises 0.1 to 10 pt. wt. of at least one crosslinker (B), 0.01 to 7 pt. wt. of a catalyst (C), 0 to 5 pt. wt. of an adhesion promoter (D), and 0.02 to 3 pt. wt. component (F).

In another aspect, the present invention provides a method of providing a cured material comprising exposing the composition to ambient air.

According to one embodiment, a method of providing a cured material comprises combining the first portion and the second portion and curing the mixture.

According to one embodiment, the composition is stored in a sealed cartridge or flexible bag having outlet nozzles for extrusion and/or shaping of the uncured composition prior to cure.

In still another aspect, the present invention provides a cured polymer material formed from the composition.

According to one embodiment, the cured polymer material is in the form of an elastomeric or duromeric seal, an adhesive, a coating, an encapsulant, a shaped article, a mold, and an impression material.

The compositions are found to exhibit good storage stability and adhere to a variety of surfaces. In one embodiment, the curable compositions exhibit excellent adherence to thermoplastic surfaces, including polyacrylate and polymethylmethacrylate (PMMA) surfaces.

DETAILED DESCRIPTION

The present invention provides a curable composition employing an iron (Fe(III)) or a bismuth (Bi(III)) complex as a condensation catalyst. The Fe(III) or Bi(III) complexes identified in the present invention in combination with an adhesion promoter and an acidic compound exhibit similar or superior curing properties as compared to compositions employing organotin compounds, such as DBTDL, in terms of accelerating moisture assisted condensation curing of silicones to result in cross-linked silicones that can be used as sealants and RTVs (Room-Temperature Vulcanized Rubber).

The non-toxic nature of these manganese compounds makes them more attractive and practical than organotin catalysts, given the forthcoming strict regulations on organotin catalysts.

The present invention provides a curable composition comprising a polymer component (A) comprising a reactive terminal silyl group, a cross-linker component (B), a catalyst component (C) comprising a Fe(III)-based complex or a Bi(III)-based complex, an adhesion promoter component (D), an optional filler component (E), and an acidic compound (F), and optionally auxiliary components (G).

The polymer component (A) may be a liquid or solid-based polymer having a reactive terminal silyl group. The polymer component (A) is not particularly limited and may be chosen from any cross-linkable polymer as may be desired for a particular purpose or intended use. Non-limiting examples of suitable polymers for the polymer component (A) include polyorganosiloxanes (A1) or organic polymers free of siloxane bonds (A2), wherein the polymers (A1) and (A2) comprise reactive terminal silyl groups. In one embodiment, the polymer component (A) may be present in an amount of from about 10 to about 90 wt. % of the curable composition. In one embodiment, the curable composition comprises about 100 pt. wt. of the polymer component (A).

As described above, the polymer component (A) may include a wide range of polyorganosiloxanes. In one embodiment, the polymer component may comprise one or more polysiloxanes and copolymers of formula (3):

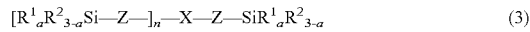
(3)

$R^1$ may be chosen from saturated $C_1$-$C_{12}$ alkyl (which can be substituted with one or more of a halogen (e.g., Cl, F, O, S or N atom), $C_5$-$C_{16}$ cycloalkyl, $C_2$-$C_{12}$ alkenyl, $C_7$-$C_{16}$ aralikyl, $C_7$-$C_{16}$ alkylaryl, phenyl, $C_2$-$C_4$ polyalkylene ether, or a combination of two or more thereof. Exemplary preferred groups are methyl, trifluoropropyl and/or phenyl groups.

$R^2$ may be a group reactive to protonated agents such as water and may be chosen from OH, $C_1$-$C_8$-alkoxy, $C_2$-$C_{18}$-alkoxyalkyl, amino, alkenyloxy, oximoalkyl, enoxyalkyl, aminoalkyl, carboxyalkyl, amidoalkyl, amidoaryl, carbamatoalkyl or a combination of two or more thereof. Exemplary groups for $R^2$ include OH, alkoxy, alkenyloxy, alkyloximo, alkylcarboxy, alkylamido, arylamido, or a combination of two or more thereof.

Z may be a bond, a divalent linking unit selected from the group of $O_{1/2}$, hydrocarbons which can contain one or more O, S or N atom, amide, urethane, ether, ester, urea units or a combination of two or more thereof. If the linking group Z is a hydrocarbon group then Z is linked to the silicon atom over a SiC bond. In one embodiment Z is chosen from a $C_1$-$C_{14}$ alkylene.

X is chosen from a polyurethane; a polyester; a polyether; a polycarbonate; a polyolefin; a polypropylene; a polyester-ether; and a polyorganosiloxane having units of $R_3SiO_{1/2}$, $R_2SiO$, $RSiO_{3/2}$, and/or $SiO_{4/2}$, where R is chosen from a $C_1$-$C_{10}$-alkyl; a $C_1$-$C_{10}$ alkyl substituted with one or more of Cl, F, N, O or S; a phenyl; a $C_7$-$C_{16}$ alkylaryl; a $C_7$-$C_{16}$ arylalkyl; a $C_2$-$C_4$ polyalkylene ether; or a combination of two or more thereof may be a divalent or multivalent polymer unit selected from the group of siloxy units linked over oxygen or hydrocarbon groups to the terminal silyl group comprising the reactive group $R^2$ as described above, polyether, alkylene, isoalkylene, polyester or polyurethane units linked over hydrocarbon groups to the silicon atom comprising one or more reactive groups $R^2$ as described above. The hydrocarbon group X can contain one or more heteroatoms such as N, S, O or P forming amides, esters, ethers urethanes, esters, ureas. In one embodiment, the average polymerization degree ($P_n$) of X should be more than 6, e.g. polyorganosiloxane units of $R_3SiO_{1/2}$, $R_2SiO$, $RSiO_{3/2}$, and/or $SiO_{4/2}$. In formula (3), n is 0-100; desirably 1, and a is 0-2, desirably 0-1.

Non-limiting examples of the components for unit X include polyoxyalkylene polymers such as polyoxyethylene, polyoxypropylene, polyoxybutylene, polyoxyethylene-polyoxypropylene copolymer, polyoxytetramethylene, or polyoxypropylene-polyoxybutylene copolymer; ethylene-propylene copolymer, polyisobutylene, polychloroprene, polyisoprene, polybutadiene, copolymer of isobutylene and isoprene, copolymers of isoprene or butadiene and acrylonitrile and/or styrene, or hydrocarbon polymer such as hydrogenated polyolefin polymers produced by hydrogenating these polyolefin polymers; polyester polymer manufactured by a condensation of dibasic acid such as adipic acid or phthalic acid and glycol, polycarbonates, or ring-opening polymerization of lactones; polyacrylic acid ester produced by radical polymerization of a monomer such as $C_2$-$C_8$-alkyl acrylates, vinyl polymers, e.g., acrylic acid ester copolymer of acrylic acid ester such as ethyl acrylate or butyl acrylate and vinyl acetate, acrylonitrile, methyl methacrylate, acrylamide or styrene; graft polymer produced by polymerizing the above organic polymer with a vinyl monomer; polysulfide polymer; polyamide polymer such as Nylon 6® produced by ring-opening polymerization of ε-caprolactam, Nylon 6.6 produced by polycondensation of hexamethylenediamine and adipic acid, etc., Nylon 12 produced by ring-opening polymerization of ε-aminolauro-lactam, copolymeric polyamides, polyurethanes, or polyureas.

Particularly suitable polymers include, but are not limited to, polysiloxanes, polyoxyalkylenes, saturated hydrocarbon polymers such as polyisobutylene, hydrogenated polybutadiene and hydrogenated polyisoprene, or polyethylene, polypropylene, polyester, polycarbonates, polyurethanes, polyurea polymers and the like. Furthermore, saturated hydrocarbon polymer, polyoxyalkylene polymer and vinyl copolymer are particularly suitable due to their low glass transition temperature which provide a high flexibility at low temperatures, i.e. below 0° C.

The reactive silyl groups in formula (3) can be introduced by employing silanes containing a functional group which has the ability to react by known methods with unsaturated hydrocarbons via hydrosilylation, or reaction of SiOH, aminoalkyl, HOOC-alkyl, HO-alkyl or HO-aryl, HS-alkyl or -aryl, Cl(O)C-alkyl or -aryl, epoxyalkyl or epoxycycloalkyl groups in the prepolymer to be linked to a reactive silyl group via condensation or ring-opening reactions. Examples of the main embodiments include the following: (i) siloxane prepolymers having a SiOH group that can undergo a condensation reaction with a silane (L-group)$SiR^1_aR^2_{3-a}$ whereby a siloxy bond ≡Si—O—$SiR^1_aR^2_{3-a}$ is formed while the addition product of the leaving group (L-group) and hydrogen is released (L-group +H); (ii) silanes having an unsaturated group that is capable of reacting via a hydrosilylation or a radical reaction with a SiH group or radically activated groups of a silane such as SiH or an unsaturated group; and (iii) silanes including organic or inorganic prepolymers having OH, SH, amino, epoxy, —COCl, —COOH groups, which can react complementarily with epoxy, isocyanato, OH, SH, cyanato, carboxylic halogenides, reactive alkylhalogenides, lactones, lactams, or amines, that is to link the reactive prepolymer with the organofunctional silanes to yield a silyl functional polymer.

Silanes suitable for method (i) include alkoxysilanes, especially tetraalkoxysilanes, di- and trialkoxysilanes, di- and triacetoxysilanes, di- and triketoximato-silanes, di- and trialkenyloxysilanes, di- and tricarbonamidosilanes, wherein the remaining residues at the silicon atom of the silane are substituted or unsubstituted hydrocarbons. Other non-limiting silanes for method (i) include alkyltrialkoxysilanes, such as vinyltrimethoxysilane, methyltrimethoxysilane, propyltrimethoxysilane aminoalkyltrimethoxysilane, ethyltriacetoxysilane, methyl- or propyltriacetoxysilane, methyltributanonoximosilane, methyltripropenyloxysilane, methyltribenzamidosilane, or methyltriacetamidosilane. Prepolymers suitable for reaction under method (i) are SiOH-terminated polyalkylsiloxanes, which can undergo a condensation reaction with a silane having hydrolysable groups attached to the silicon atom. Exemplary SiOH-terminated polyalkydisiloxanes include polydimethylsilaxanes.

Suitable silanes for method (ii) include alkoxysilanes, especially trialkoxysilanes (HSi(OR)$_3$) such as trimethoxysilane, triethoxysilane, methyldiethoxysilane, methyldimethoxysilane, and phenyldimethoxysilane; methyldiacetoxysilane and phenyldiacetoxysilane. Hydrogenchlorosilanes are in principle possible but are less desirable due to the additional replacement of the halogen through an alkoxy, acetoxy group, etc. Other suitable silanes include organofunctional silanes having unsaturated groups which can be activated by radicals, such as vinyl, allyl, mercaptoalkyl, or acrylic groups. Non-limiting examples include vinyltrimethoxysilane, mercaptopropyltrimethoxysilane, methyacryloxypropyltrimethoxysilane. Prepolymers suitable for reaction under method (ii) include vinyl terminated polyalkylsiloxanes, preferably polydimethylsiloxanes, hydrocarbons with unsaturated groups which can undergo hydrosilylation or can undergo radically induced grafting reactions with a corresponding organofunctional group of a silane comprising, for example, unsaturated hydrocarbon or a —SiH group.

Another method for introducing silyl groups into hydrocarbon polymers can be the copolymerization of unsaturated hydrocarbon monomers with the unsaturated groups of silanes. The introduction of unsaturated groups into a hydrocarbon prepolymer may include, for example, the use of alkenyl halogenides as chain stopper after polymerization of the silicon free hydrocarbon moiety.

Desirable reaction products between the silanes and prepolymers include the following structures:

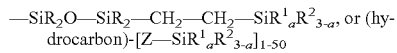
—SiR$_2$O—SiR$_2$—CH$_2$—CH$_2$—SiR$^1_a$R$^2_{3-a}$, or (hydrocarbon)-[Z—SiR$^1_a$R$^2_{3-a}$]$_{1-50}$ Suitable silanes for method (iii) include, but are not limited to, alkoxysilanes, especially silanes having organofunctional groups to be reactive to —OH, —SH, amino, epoxy, —COCl, or —COOH.

In one embodiment, these silanes have an isocyanatoalkyl group such as gamma-isocyanatopropyltrimethoxysilane, gamma-isocyanatopropylmethyldimethoxysilane, gamma-isocyanatopropyltriethoxysilane, gamma-glycidoxypropylethyldimethoxysilane, gamma-glycidoxypropyltrimethoxysilane, gamma-glycidoxypropyltrimethoxysilane, gamma-(3,4-epoxycyclohexyl)ethyltrimethoxysilane, epoxylimonyltrimethoxysilane, N-(2-aminoethyl)-aminopropyltrimethoxysilane gamma-aminopropyltriethoxysilane, gamma-aminopropyltrimethoxysilane, gamma-aminopropylmethyldimethoxysilane, gamma-aminopropylmethyldiethoxysilane, etc.

In one embodiment, it is desirable to select either blocked amines or isocyanates (Z'—X)$_n$—Z' for carrying out first a complete mixing and then the following coupling reaction. Examples of blocking agents are disclosed in EP 0947531 and other blocking procedures that employ heterocyclic nitrogen compounds such as caprolactam or butanone oxime, or cyclic ketones referred to in U.S. Pat. No. 6,827,875 both of which are incorporated herein by reference in their entirety.

Examples of suitable prepolymers for a reaction under method (iii) include, but are not limited to, polyalkylene oxides having OH groups, preferably with a high molecular weight (Mw) (weight average molecular weight>6000 g/mol) and a polydispersity $M_w/M_n$ of less than 1.6; urethanes having remaining NCO groups, such as NCO functionalized polyalkylene oxides, especially blocked isocyanates. Prepolymers selected from the group of hydrocarbons having —OH, —COOH, amino, epoxy groups, which can react complementarily with an epoxy, isocyanato, amino, carboxyhalogenide or halogenalkyl group of the corresponding silane having further reactive groups useful for the final cure.

Suitable isocyanates for the introduction of a NCO group into a polyether may include toluene diisocyanate, diphenylmethane diisocyanate, or xylene diisocyanate, or aliphatic polyisocyanate such as isophorone diisocyanate, or hexamethylene diisocyanate.

The polymerization degree of the unit X depends on the requirements of viscosity and mechanical properties of the cured product. If X is a polydimethylsiloxane unit, the average polymerization degree based on the number average molecular weight $M_n$ is preferably 7 to 5000 siloxy units, preferably 200-2000 units. In order to achieve a sufficient tensile strength of >5 MPa, an average polymerization degree $P_n$ of >250 is suitable whereby the polydimethylsiloxanes have a viscosity of more than 300 mPa·s at 25° C. If X is a hydrocarbon unit other than a polysiloxane unit, the viscosity with respect to the polymerization degree is much higher.

Examples of the method for synthesizing a polyoxyalkylene polymer include, but are not limited to, a polymerization method using an alkali catalyst such as KOH, a polymerization method using a transition metal compound porphyrin complex catalyst such as complex obtained by reacting an organoaluminum compound, a polymerization method using a composite metal cyanide complex catalyst disclosed, e.g., in U.S. Pat. No. 3,427,256; U.S. Pat. No. 3,427,334; U.S. Pat. No. 3,278,457; U.S. Pat. No. 3,278,458; U.S. Pat. No. 3,278,459; U.S. Pat. No. 3,427,335; U.S. Pat. No. 6,696,383; and U.S. Pat. No. 6,919,293.

If the group X is selected from hydrocarbon polymers, then polymers or copolymers having isobutylene units are particularly desirable due to its physical properties such as excellent weatherability, excellent heat resistance, and low gas and moisture permeability.

Examples of the monomers include olefins having 4 to 12 carbon atoms, vinyl ether, aromatic vinyl compound, vinylsilanes, and allylsilanes. Examples of the copolymer component include 1-butene, 2-butene, 2-methyl-1-butene, 3-methyl-1-butene, pentene, 4-methyl-1-pentene, hexene, vinylcyclohexene, methyl vinyl ether, ethyl vinyl ether, isobutyl vinyl ether, styrene, alpha-methylstyrene, dimethylstyrene, beta-pinene, indene, and for example, but not limited to, vinyltrialkoxysilanes, e.g. vinyltrimethoxysilane, vinylmethyldichlorosilane, vinyldimethylmethoxysilane, divinyldichlorosilane, divinyldimethoxysilane, allyltrichlorosilane, allylmethyldichlorosilane, allyldimethylmethoxysilane, diallyldichlorosilane, diallyldimethoxysilane, gamma-methacryloyloxypropyltrimethoxysilane, and gamma-methacryloyloxy-propyl-methyldimethoxysilane.

In one embodiment, the polymer component (A) may be a polymer of formula (4):

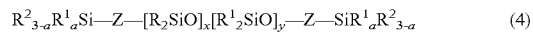
$$R^2_{3-a}R^1_aSi—Z—[R_2SiO]_x[R^1_2SiO]_y—Z—SiR^1_aR^2_{3-a} \quad (4)$$

where $R^1$, $R^2$, and Z are defined as above with respect to formula (3); R is $C_1$-$C_6$-alkyl (an exemplary alkyl being methyl); a is 0-2, x is 0 to about 10,000; preferably 11 to about 2500; and y is 0 to about 1,000; preferably 0 to 500. In one embodiment, Z in a compound of formula (4) is a bond or a divalent $C_2$ to $C_{14}$-alkylene group, especially preferred is —$C_2H_4$—.

Non-limiting examples of suitable polysiloxane-containing polymers (A1) include, for example, silanol-stopped polydimethylsiloxane, silanol or alkoxy-stopped polyorganosiloxanes, e.g., methoxystopped polydimethylsiloxane, alkoxy-stopped polydimethylsiloxane-polydiphenylsiloxane copolymer, and silanol or alkoxy-stopped fluoroalkyl-substituted siloxanes such as poly(methyl 3,3,3-trifluoropropyl) siloxane and poly(methyl 3,3,3-trifluoropropyl)siloxane-polydimethyl siloxane copolymer. The polyorganosiloxane component (A1) may be present in an amount of about 10 to about 90 wt. of the composition or 100 pt. wt. In one preferred embodiment, the polyorganosiloxane component has an average chain length in the range of about 10 to about 2500 siloxy units, and the viscosity is in the range of about 10 to about 500,000 mPa·s at 25° C.

Alternatively, the composition may include silyl-terminated organic polymers (A2) that are free of siloxane units, and which undergo curing by a condensation reaction comparable to that of siloxane containing polymers (A1). Similar to the polyorganosiloxane polymer (A1), the organic polymers (A2) that are suitable as the polymer component (A) include a terminal silyl group. In one embodiment, the terminal silyl group may be of the formula (5):

where $R^1$, $R^2$, and a are as defined above.

Examples of suitable siloxane free organic polymers include, but are not limited to, silylated polyurethane (SPUR), silylated polyester, silylated polyether, silylated polycarbonate, silylated polyolefins like polyethylene, polypropylene, silylated polyesterether and combinations of two or more thereof. The siloxane-free organic polymer may be present in an amount of from about 10 to about 90 wt. % of the composition or about 100 pt. wt.

In one embodiment, the polymer component (A) may be a silylated polyurethane (SPUR). Such moisture curable compounds are known in the art in general and can be obtained by various methods including (i) reacting an isocyanate-terminated polyurethane (PUR) prepolymer with a suitable silane, e.g., one possessing both hydrolyzable functionality at the silicon atom, such as, alkoxy, etc., and secondly active hydrogen-containing functionality such as mercaptan, primary or secondary amine, preferably the latter, etc., or by (ii) reacting a hydroxyl-terminated PUR (polyurethane) prepolymer with a suitable isocyanate-terminated silane, e.g., one possessing one to three alkoxy groups. The details of these reactions, and those for preparing the isocyanate-terminated and hydroxyl-terminated PUR prepolymers employed therein can be found in, amongst others: U.S. Pat. Nos. 4,985,491; 5,919,888; 6,207,794; 6,303,731; 6,359,101; and 6,515,164 and published U.S. Patent Application Nos. 2004/0122253 and US 2005/0020706 (isocyanate-terminated PUR prepolymers); U.S. Pat. Nos. 3,786,081 and 4,481,367 (hydroxyl-terminated PUR prepolymers); U.S. Pat. Nos. 3,627,722; 3,632, 557; 3,971,751; 5,623,044; 5,852,137; 6,197,912; and 6,310, 170 (moisture-curable SPUR (silane modified/terminated polyurethane) obtained from reaction of isocyanate-terminated PUR prepolymer and reactive silane, e.g., aminoalkoxysilane); and, U.S. Pat. Nos. 4,345,053; 4,625,012; 6,833, 423; and published U.S. Patent Application 2002/0198352 (moisture-curable SPUR obtained from reaction of hydroxyl-terminated PUR prepolymer and isocyanatosilane). The entire contents of the foregoing U.S. patent documents are incorporated by reference herein. Other examples of moisture curable SPUR materials include those described in U.S. Pat. No. 7,569,653, the disclosure of which is incorporated by reference in its entirety.

The polysiloxane composition may further include a crosslinker or a chain extender as component (B). In one embodiment, the crosslinker is of the formula (6):

wherein $R^2$ may be as described above, $R^1$ may be as described above, and a is 0-3. Alternatively, the cross-linker component may be a condensation product of formula (6) wherein one or more but not all $R^2$ groups are hydrolyzed and released in the presence of water and then intermediate silanols undergo a condensation reaction to give a Si—O—Si bond and water. The average polymerization degree can result in a compound having 2-10 Si units.

As used herein, the term crosslinker includes a compound including an additional reactive component having at least two hydrolysable groups and less than three silicon atoms per molecule not defined under (A). In one embodiment, the crosslinker or chain extender may be chosen from an alkoxysilane, an alkoxysiloxane, an oximosilane, an oximosiloxane, an enoxysilane, an enoxysiloxane, an aminosilane, a carboxysilane, a carboxysiloxane, an alkylamidosilane, an alkylamidosiloxane, an arylamidosilane, an arylamidosiloxane, an alkoxyaminosilane, an alkaryaminosiloxane, an alkoxycarbamatosilane, an alkoxycarbamatosiloxane, an imidatosilane, a ureidosilane, an isocyanatosilane, a thioisocyanatosilane, and combinations of two or more thereof. Examples of suitable cross-linkers include, but are not limited to, tetraethylorthosilicate (TEOS); methyltrimethoxysilane (MTMS); methyltriethoxysilane; vinyltrimethoxysilane; vinyltriethoxysilane; methylphenyldimethoxysilane; 3,3,3-trifluoropropyltrimethoxysilane; methyltriacetoxysilane; vinyltriacetoxysilane; ethyltriacetoxysilane; di-butoxydiacetoxysilane; phenyltripropionoxysilane; methyltris(methylethylketoxime)silane; vinyltris(methylethylketoxime)silane; 3,3,3-trifluoropropyltris(methylethylketoxime)silane; methyltris(isopropenoxy)silane; vinyltris(isopropenoxy)silane; ethylpolysilicate; dimethyltetraacetoxydisiloxane; tetra-n-propylorthosilicate; methyldimethoxy(ethylmethylketoximo)silane; methylmethoxybis-(ethylmethylketoximo)silane; methyldimethoxy(acetaldoximo)silane; methyldimethoxy(N-methylcarbamato)silane; ethyldimethoxy(N-methylcarbamato)silane; methyldimethoxyisopropenoxysilane; trimethoxyisopropenoxysilane; methyltri-iso-propenoxysilane; methyldimethoxy(but-2-ene-2-oxy)silane; methyldimethoxy(1-phenylethenoxy)silane; methyldimethoxy-2(1-carboethoxypropenoxy)silane; methylmethoxydi-N-methylaminosilane; vinyldimethoxymethylaminosilane; tetra-N,N-diethylaminosilane; methyldimethoxymethylaminosilane; methyltricyclohexylaminosilane; methyldimethoxyethylaminosilane; dimethyldi-N,N-dimethylaminosilane; methyldimethoxyisopropylaminosilane; dimethyldi-N,N-diethylaminosilane; ethyldimethoxy(N-ethylpropionamido)silane; methyldimethoxy(N-methylacetamido)silane; methyltris(N-methylacetamido)silane; ethyldimethoxy(N-methylacetamido)silane; methyltris(N-methylbenzamido)silane; methylmethoxybis(N-methylacetamido)silane; methyldimethoxy(caprolactamo)silane; trimethoxy(N-methylacetamido) silane; methyldimethoxyethylacetimidatosilane; methyldimethoxypropylacetimidatosilane; methyldimethoxy(N,N',N'-trimethylureido)silane; methyldimethoxy(N-allyl-N',N'-dimethylureido)silane; methyldimethoxy(N-phenyl-N',N'-dimethylureido)silane; methyldimethoxyisocyanatosilane; dimethoxydiisocyanatosilane; methyl dimethoxythioisocyanatosilane; methylmethoxydithioisocyanatosilane, or combinations of two or more thereof. In one embodiment, the crosslinker may be present in an amount from about 1 to about 10 wt. % of the composition or from about 0.1 to about 10 pt. wt. per 100 pt. wt. of the polymer component (A). In another embodiment, the crosslinker may be present in an amount from about 0.1 to about 5 pt. wt. per 100 pt. wt. of the polymer component (A). In still another embodiment, the crosslinker may be present in an amount from about 0.5 to about 3 pt. wt. per 100 pt. wt. of the polymer component (A). Here as elsewhere in the specification and claims, numerical values may be combined to form new or undisclosed ranges.

Additional alkoxysilanes in an amount greater than 0.1 wt. % of component and (A) that are not consumed by the reaction between the prepolymer Z'—X—Z' and which comprise additional functional groups selected from $R^4$ can also work as an adhesion promoter and are defined and counted under component (D).

The curable compositions further comprise an organometal catalyst (C) chosen from a Fe(III) complex or a Bi(III) complex. The inventors have unexpectedly found that Fe(III) and Bi(III) complexes, when used with an adhesion promoter and an acidic compound in accordance with aspects of the invention, exhibit excellent catalytic activity and are found to work satisfactorily in most of the compositions, e.g., typical sealant RTV1 or RTV2 formulations, comprising polymers having reactive terminal groups, which may additionally contain other ingredients. In comparison to DBTDL, which is a free flowing liquid, the Fe(III) or Bi(III) complexes may be either solid or liquid in nature. In the case of solid Fe(III) or Bi(III) complexes, these are usually dispersed with the aid of an organic solvent.

In one embodiment, the catalyst component (C) is a Fe(III) complex of the Formula (1), a Bi(III) complex of the Formula (2), or a combination thereof:

  (1),

  (2), wherein Y is a chelating ligand, A is an anion, and c=0-2.

The chelating ligand Y may be chosen from diketonates, diamines, triamines, aminoacetates, nitriloacteates, bipyridins, glyoximes, a carboxylate, combinations of two or more thereof, and the like. Examples of suitable chelating ligands include, but are not limited to, acetylacetonate-2,4-pentanedione ("AA" or "acac"); hexanedione-2,4; heptanedione-2,4; heptanedione-3,5; ethyl-3-pentanedione-2,4; methyl-5-hexanedione-2,4; octanedione-2,4; octanedione-3,5; dimethyl-5,5 hexanedione-2,4; methyl-6-heptanedione-2,4; dimethyl-2,2-nonanedione-3,5; dimethyl-2,6-heptanedione-3,5; 2-acetylcyclohexanone (Cy-acac); 2,2,6,6-tetramethyl-3,5-heptanedione (t-Bu-acac); 1,1,1,5,5,5-hexafluoro-2,4-pentanedione (F-acac)]; benzoylacetone; dibenzoylmethane; 3-methyl-2,4-pentadione; 3-acetyl-pentane-2-one; 3-acetyl-2-hexanone; 3-acetyl-2-heptanone; 3-acetyl-5-methyl-2-hexanone; stearoylbenzoylmethane; octanoylbenzoylmethane; 4-t-butyl-4'-methoxy-dibenzoylmethane; 4,4'-dimethoxy-dibenzoylmethane; 4,4'-di-tert-butyl-dibenzoylmethane; hexafluoroacetylacetone, or a combination of two or more thereof.

In one embodiment, the anion A is selected from group which consists of substituted, unsubstituted $C_4$-$C_{25}$-alkyl-, $C_7$-$C_{25}$-arylalkyl, $C_7$-$C_{25}$-alkylaryl and $C_6$-$C_{10}$-aryl carboxylate anions. The anion may be a carboxylate chosen from pentanoate, hexoate, heptoate, octoate, 2-ethyl hexanoate, neodeconate, etc., or a combination of two or more thereof.

The anion A in formulas (1) or (2) is not particularly limited and may be chosen from anions including, but not limited to, halides, hydroxide, oxide, peroxide, ozonide, hydrosulfide, alkoxides, alkyl thio, nitride, acetate, amide, carboxylate, cyanide, cyanate, thiocyanate, carbonate, hydrogen carbonate and the like. Some specific examples of suitable anions include, but are not limited to, $F^-$, $Cl^-$, $(I_3)^-$, $[ClF_2]^-$, $[IF_6]^-$, $(ClO)^-$, $(ClO_2)^-$, $(ClO_3)^-$, $(ClO_4)^-$, $(OH)^-$, $(SH)^-$, $(SeH)^-$, $(O_2)^-$, $(O_3)^-$, $(HS_2)^-$, $(CH_3O)^-$, $(C_2H_5O)^-$, $(C_3H_7O)^-$, $(CH_3S)^-$, $(C_2H_5S)^-$, $(C_2H_4ClO)^-$, $(C_6H_5O)^-$, $(C_6H_5S)^-$, $[C_6H_4(NO_2)O]^-$, $(HCO_2)^-$, $(C_7H_{15}CO_2)^-$, $(CH_3CO_2)^-$, $(CH_3CH_2CO_2)^-$, $(N_3)^-$, $(CN)^-$, $(NCO)^-$, $(NCS)^-$, $(NCSe)^-$, $(NH_2)^-$, $(PH_2)^-$, $(ClHN)^-$, $(Cl_2N)^-$, $(CH_3NH)^-$, $(HN=N)''$, $(H_2N—NH)^-$, $(HP=P)^-$, $(H_2PO)^-$, $(H_2PO_2)^-$, and the like. In one embodiment, the anion A is chosen from a branched $C_4$-$C_{25}$-alkyl carboxylic acid.

In one embodiment, the catalyst compound (C) comprises Fe(III) penta-2,4-dionate. In another embodiment, the catalyst component (C) comprises Fe(III) 3-methyl-penta-2,4-dionate. In still another embodiment, the catalyst component (C) comprises Bi(III)-octoate. In another embodiment, the catalyst component (C) comprises Bi(III) neodecanoate. In another embodiment, the catalyst compound (C) comprises Bi(III) 2-ethylhexanoate.

In one embodiment, the Fe(III) or Bi(III) complex may be added to the composition in an amount of from about 0.01 to about 7.0 pt. wt. related to 100 part per weight of component (A). In another embodiment the Fe(III) or Bi(III) complex may be added in an amount of from about 0.1 to about 5.0 pt. wt. In still another embodiment, the Fe(III) or Bi(III) complex may be added in an amount of from about 0.15 to about 2.5 pt. wt. In still another embodiment, the Fe(III) or Bi(III) complex may be present in an amount of about 0.2 to about 0.5 pt. wt. per 100 pt. wt. of component (A). An increase in the amount of Fe(III) or Bi(III) complex as a catalyst may increase the cure rate of curing the surface and decrease the cure time for a tack-free surface and the complete cure through the bulk. Furthermore, the amount of the Fe(III) or Bi(III) complex added to the composition may affect the viscosity of the composition. Particularly, an increase in the amount of the Fe(III) or Bi(III) complex may increase the final viscosity of the composition, which is less desirable.

The composition furthers include an adhesion promoter component (D) that is different to component (A) or (B). In one embodiment, the adhesion promoter (D) may be an organofunctional silane comprising the group $R^4$, e.g., aminosilanes, and other silanes that are not identical to the silanes of component (B), or are present in an amount which exceeds the amount of silanes necessary for endcapping the polymer (A). The amount of non-reacted silane (B) or (D) in the reaction for making (A) can be defined in that after the endcapping reaction the free silanes are evaporated at a higher temperature up to 200° C. and vacuum up to 1 mbar to be more than 0.1 wt. % of (A).

Thus, some selected amines can advantageously be added to fine-tune the rate of the metal complex catalyzed condensation curing of silicone/non-silicone polymer containing reactive silyl groups, as desired.

In one embodiment, the composition comprises an adhesion promoter (D) comprising a group $R^4$ as described by the general formula (7):

$$R^4_e R^1_d Si(OR^3)_{4-d-e} \quad (7)$$

where $R^4$ is $E-(CR^5_2)_f-W-(CH_2)_f-$; $R^1$ is as described above; d is 0, 1 or 2; e=1, 2 or 3; d+e=1 to 2; and f is 0 to 8, and may be identical or different.

Non-limiting examples of suitable compounds include:

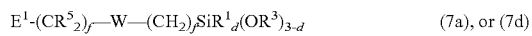
(7a), or (7d)

(7b) or (7f)

where p=2-3.

The group E may be selected from either a group $E^1$ or $E^2$. $E^1$ may be selected from a monovalent group comprising amine, $-NH_2$, $-NHR$, $-(NHC_2H_5)_{1-10}NHR$, $NHC_6H_5$, halogen, pseudohalogen, unsaturated aliphatic group with up to 14 carbon atoms, epoxy-group-containing aliphatic group with up to 14 carbon atoms, cyanurate-containing group, and an isocyanurate-containing group.

$E^2$ may be selected from a group comprising of a di- or multivalent group consisting of amine, polyamine, isocyanurate-containing and an isocyanurate-containing group, sulfide, sulfate, phosphate, phosphite and a polyorganosiloxane group, which can contain $R^4$ and $OR^3$ groups; W is selected from the group consisting of a single bond, a heteroatomic group selected from $-COO-$, $-O-$, epoxy, $-S-$, $-CONH-$, $-HN-CO-NH-$ units; $R^5$ is selected from hydrogen and R as defined above, $R^1$ may be identical or different as defined above, $R^3$ is selected from the group, which consists of $C_1$-$C_8$-alkoxy, such as methoxy, ethoxy, $C_3$-$C_{12}$-alkoxyalkyl, $C_2$-$C_{22}$-alkylcarboxy and $C_4$-$C_{100}$-polyalkylene oxide may be identical or different.

Non-limiting examples of component (D) include:

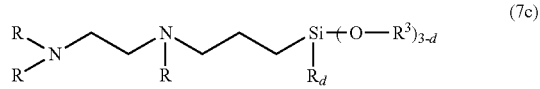
(7c)

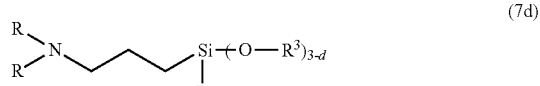
(7d)

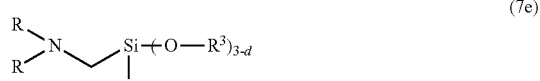
(7e)

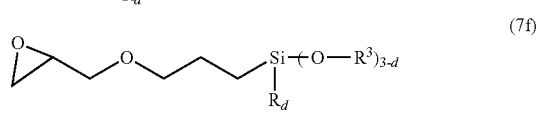
(7f)

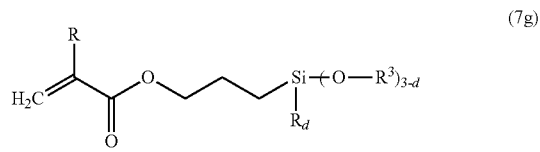
(7g)

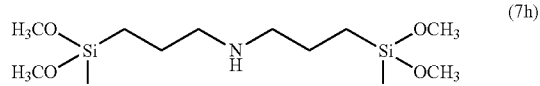
(7h)

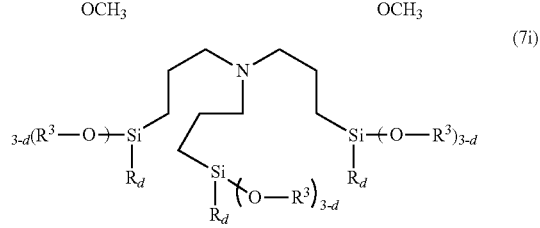
(7i)

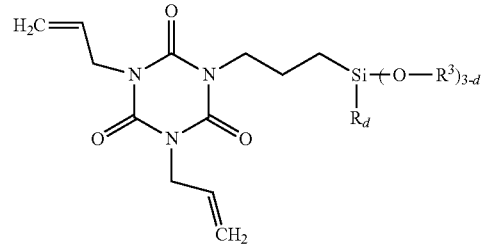
(7j)

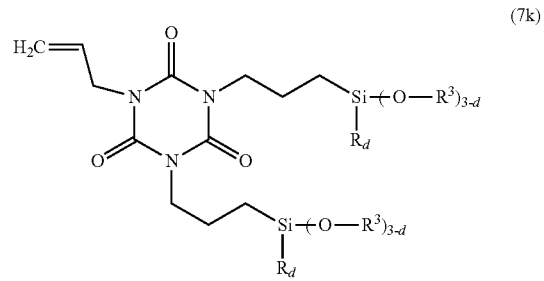
(7k)

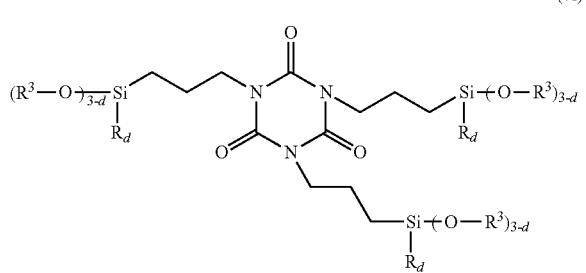
(7l)

wherein R and d are as defined above. Examples of component (D) include compounds of the formulas (7a-7k). Furthermore the formula (7b) of compounds (D) shall comprise compounds of the formula (7l):

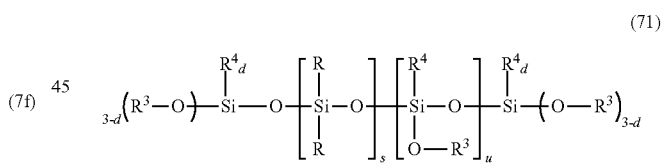
(7l)

wherein: R, $R^1$, $R^3$, and $R^4$ are as defined above; $R^6$ is hydrogen, R, linear and branched $C_3$-$C_{16}$ alkyl, $C_5$-$C_{14}$ cycloalkyl, phenyl, and phenyl substituted with $C_1$-$C_8$ alkyl; s is 0-6 (and in one embodiment desirably 0); u is 0-10 (in one embodiment desirably 0-5); and s+u is 10 or less. In one embodiment, $R^4$ is selected from:

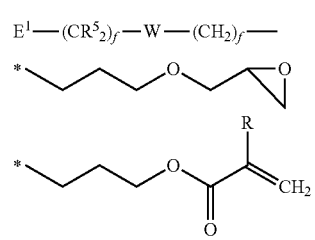

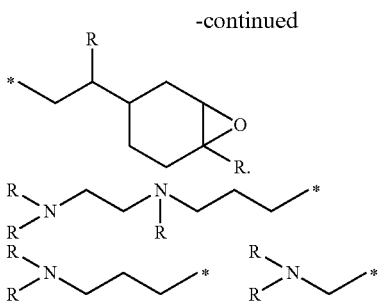

An exemplary group of adhesion promoters are selected from the group which consists of amino group-containing silane coupling agents, which can also be used as the cure rate modifying component (F). The amino group-containing silane adhesion promoter agent (D) is a compound having a group containing a silicon atom bonded to a hydrolyzable group (hereinafter referred to as a hydrolyzable group attached to the silicon atom) and an amino group. Specific examples thereof include the same silyl groups with hydrolyzable groups described above. Among these groups, the methoxy group and ethoxy group are particularly suitable. The number of the hydrolyzable groups may be 2 or more, and particularly suitable are compounds having 3 or more hydrolyzable groups.

Examples of other suitable adhesion promoter (D) include, but are not limited to N-(2-aminoethyl)aminopropyltrimethoxysilane gamma-aminopropyltriethoxysilane, gamma-aminopropyltrimethoxysilane, bis(gamma-trimethoxysilypropyl)amine, N-phenyl-gamma-aminopropyltrimethoxysilane, triaminofunctionaltrimethoxysilane, gamma-aminopropyl-methyldimethoxysilane, gamma-aminopropylmethyldiethoxysilane, methacryloxypropyltrimethoxysilane, methyl aminopropyltrimethoxysilane, gamma-glycidoxypropylethyldimethoxysilane, gamma-glycidoxypropyltrimethoxysilane, gamma-glycidoxyethyltrimethoxysilane, gamma-(3,4-epoxycyclohexyl)ethyltrimethoxysilane, beta-(3,4-epoxycyclohexyl)ethylmethyl-dimethoxysilane, epoxylimonyltrimethoxysilane, isocyanatopropyltriethoxysilane, isocyanatopropyltrimethoxysilane, isocyanatopropylmethyldimethoxysilane, beta-cyano-ethyl-trimethoxysilane, gamma-acryloxypropyl-trimethoxy-silane, gamma-methacryloxypropyl-methyldimethoxysilane, alpha, omega-bis-(aminoalkyl-diethoxysilyl)-polydimethylsiloxanes (Pn=1-7), alpha, omega-bis-(aminoalkyl-diethoxysilyl)-octa-methyltetrasiloxane, 4-amino-3,3,-dimethyl-butyl-trimethoxysilane, and N-ethyl-3-tri-methoxy-silyl-2-methyl-propanamine, 3-(diethyl-aminopropyl)-trimethoxysilane combinations of two or more thereof, and the like. Particularly suitable adhesion promoters include bis(alkyltrialkoxysilyl)amines and tris(alkyltrialkoxysilyl)amines including, but not limited to, bis(3-propyltrimethoxysilyl)amine and tris(3-propyltrimethoxysilyl)amine.

Also it is possible to use derivatives obtained by modifying them, for example, amino-modified silyl polymer, silylated amino polymer, unsaturated aminosilane complex, phenylamino long-chain alkyl silane and aminosilylated silicone. These amino group-containing silane coupling agents may be used alone, or two or more kinds of them may be used in combination.

The curable compositions of the present invention may further comprise an alkoxysilane or blend of alkoxysilanes as an adhesion promoter (D). The adhesion promoter may be a combination blend of N-2-aminoethyl-3-aminopropyltrimethoxysilane and 1,3,5-tris(trimethoxy-silylpropyl)isocyanurate and others.

The adhesion promoter (D) may be present in an amount of from about 0.1 to about 5.0 pt. wt. based on 100 parts of the polymer component (A). In one embodiment, the adhesion promoter may be present in an amount of from about 0.15 to about 2.0 pt. wt. In another embodiment, the adhesion promoter may be present in an amount of from about 0.5 to about 1.5 pt. wt of the polymer component (A). This defines the amount of (D) in composition of (A) wherein the content of free silanes coming from the endcapping of polymer (A) is smaller than 0.1 wt. %.

The present compositions may further include a filler component (E). The filler component(s) (E) may have different functions, such as to be used as reinforcing or semi-reinforcing filler, i.e., to achieve higher tensile strength after curing having in addition the ability to increase the viscosity establish pseudoplasticity/shear thinning, and thixotropic behavior as well as non-reinforcing fillers acting mainly as a volume extender. The reinforcing fillers are characterized by having a specific surface area of more than 50 $m^2/g$ related BET-surface, whereby the semi-reinforcing fillers have a specific surface area in the range of 10-50 $m^2/g$. So-called extending fillers have preferably a specific surface of less than 10 $m^2/g$ according to the BET-method and an average particle diameter below 100 p.m. In one embodiment, the semi-reinforcing filler is a calcium carbonate filler, a silica filler, or a mixture thereof. Examples of suitable reinforcing fillers include, but are not limited to fumed silicas or precipitated silica, which can be partially or completely treated with organosilanes or siloxanes to make them less hydrophilic and decrease the water content or control the viscosity and storage stability of the composition. These fillers are named hydrophobic fillers. Tradenames are Aerosil®, HDK®, Cab-O-Sil® etc.

Examples of suitable extending fillers include, but are not limited to, ground silicas (Celite™), precipitated and colloidal calcium carbonates (which are optionally treated with compounds such as stearate or stearic acid); reinforcing silicas such as fumed silicas, precipitated silicas, silica gels and hydrophobized silicas and silica gels; crushed and ground quartz, cristobalite, alumina, aluminum hydroxide, titanium dioxide, zinc oxide, diatomaceous earth, iron oxide, carbon black, powdered thermoplastics such as acrylonitrile, polyethylene, polypropylene, polytetrafluoroethylene and graphite or clays such as kaolin, bentonite or montmorillonite (treated/untreated), and the like.

The type and amount of filler added depends upon the desired physical properties for the cured silicone/non-silicone composition. As such, the filler may be a single species or a mixture of two or more species. The extending fillers can be present from about 0 to about 300 wt. % of the composition related to 100 parts of component (A). The reinforcing fillers can be present from about 5 to about 60 wt. % of the composition related to 100 parts of component (A), preferably 5 to 30 wt. %.

The inventive compositions further comprise an acidic compound (F), which, in conjunction with the adhesion promoter and Fe(III) or Bi(III) catalyst, has been found accelerate curing (as compared to curing in the absence of such compounds). The component (F) may be present in an amount of from about 0.01 to about 5 wt. % of the composition. In another embodiment 0.01 to about 8 parts per weight (pt. wt.) per 100 pt. wt. of component (A) are used, more preferably 0.02 to 3 pt. wt. per 100 pt. wt. of component (A) and most preferably 0.02 to 1 pt. wt. per 100 pt. wt. of component (A) are used.

The acidic compounds (F) may be chosen from various phosphate esters, phosphonates, phosphites, phosphines, sulfites, pseudohalogenides, branched alkyl carboxylic acids, combinations of two or more thereof, and the like. Without being bound to any particular theory, the acidic compounds (F) may, in one embodiment, be useful as stabilizers in order to ensure a longer storage time when sealed in a cartridge before use in contact with ambient air. Especially alkoxy-terminated polysiloxanes can lose the ability to cure after storage in a cartridge and show e.g. decreased hardness under curing conditions. It may, therefore be useful to add compounds of the formula (8), which can extend storage time or ability to cure over months.

$$O=P(OR^7)_{3-r}(OH)_r \quad (8)$$

whereby r is 0, 1 or 2, and $R^7$ is selected from the group a linear or branched and optionally substituted $C_1$-$C_{30}$-alkyl groups, linear or branched, $C_5$-$C_{14}$-cycloalkyl groups, $C_6$-$C_{14}$-aryl groups, $C_6$-$C_{31}$ alkylaryl groups, linear or branched $C_2$-$C_{30}$-alkenyl groups or linear or branched $C_1$-$C_{30}$-alkoxy-alkyl groups, $C_4$-$C_{300}$-polyalkenylene oxide groups (polyethers), such as Marlophor® N5 acid, triorganylsilyl- and diorganyl ($C_1$-$C_8$)-alkoxysilyl groups. The phoshates can include also mixtures of primary and secondary esters. Non-limiting examples of suitable phosphonates include 1-hydroxyethane-(1,1-diphosphonate) (HEDP), amino-trimethylene phosphonate (ATMP), nitrolotris(methylphosphonate) (NTMP), diethylenetriamine-pentakismethylene phosphonate (DTPMP), 1,2-diaminoethane-tetrakismethylene phosphonate (EDTMP), and phosphonobutanetricarbonate (PBTC).

In another embodiment, a compound of the formula $O=P(OR^7)_{2-t}(OH)_t$ may be added where t is 1 or 2, and $R^7$ is as defined above or di- or multivalent hydrocarbons with one or more amino group.

Another type are phosphonic acid compounds of the formula $O=PR^7(OH)_2$ such as alkyl phosphonic acids preferably hexyl or octyl phosphonic acid.

In one embodiment, the acidic compound may be chosen from a mono ester of a phosphate; a phosphonate of the formula $(R^3O)PO(OH)_2$, $(R^3O)P(OH)_2$, or $R^3P(O)(OH)_2$ where $R^3$ is a $C_1$-$C_{18}$-alkyl, a $C_2$-$C_{20}$-alkoxyalkyl, phenyl, a $C_7$-$C_{12}$-alkylaryl, a poly($C_2$-$C_4$-alkylene) oxide ester or its mixtures with diesters, etc.

In another embodiment, the acidic compound is a branched alkyl $C_4$-$C_{19}$-alkyl carboxylic acids, including $C_5$-$C_{19}$ acids with alpha tertiary carbon, or a combination of two or more thereof. Examples of such suitable compounds include, but are not limited to, Versatic™ Acid, Laurie Acid, Steric Acid, etc. In one embodiment, the acidic compound may be a mixture comprising branched alkyl carboxylic acids. In one embodiment, the acidic compound is a mixture of mainly tertiary aliphatic $C_{10}$-carboxylic acids.

Applicants have found that the combination of a Fe(III) or Bi(III) catalyst and an acidic compound may provide a curable composition that provides a cured polymer exhibiting a tack-free time, hardness, and/or cure time comparable to compositions made using tin catalysts, but that provide better adhesion compared to materials made using tin catalysts.

In an exemplary embodiment, the catalyst (C) comprises a complex $Fe^{III}Y_{3-c}A_c$ whereby c is $=0$ and Y is 3-methyl-2,4 pentadionate. In another exemplary embodiment, the catalyst (C) comprises a complex $Bi^{III}Y_{3-c}A_c$ whereby c is $=3$ and the anion A is a branched C4-C19-alkyl carboxylate, such as, for example, 2-ethylhexanoate.

Generally, the acidic component (F) is added in a molar ratio of less than 1 with respect to catalyst (C). In embodiments, the acidic component (F) is added in a molar ratio of (F):(C) of 1:10 to 1:4.

The curable composition may also include auxiliary substances (G) such as plasticizers, pigments, stabilizers, antimicrobial or fungicides, biocides and/or solvents. Preferred plastizers for reactive polyorganosiloxanes (A) are selected from the group of polyorganosiloxanes having chain length of 10-300 siloxy units. Preferred are trimethylsilyl terminated polydimethylsiloxanes having a viscosity of 100-1000 mPa·s at 25° C. The choice of optional solvents (dispersion media or extenders) may have a role in assuring uniform dispersion of the catalyst, thereby altering curing speed. Such solvents include polar and non-polar solvents such as toluene, hexane, chloroform, methanol, ethanol, isopropyl alcohol, acetone, methylethyl ketone, dimethylformamide (DMF), dimethyl sulfoxide (DMSO). Water can be an additional component (G) to accelerate fast curing 2 part compositions RTV 2-K, whereby the water can be in one part of the 2 compositions. Particularly suitable non-polar solvents include, but are not limited to, toluene, hexane and the like if the solvents should evaporate after cure and application. In another embodiment, the solvents include high boiling hydrocarbons such as alkylbenzenes, phtalic acid esters, arylsulfonic acid esters, trialkyl- or triarylphosphate esters, which have a low vapor pressure and can extend the volume providing lower costs. Examples cited by reference may be those of U.S. Pat. No. 6,599,633; U.S. Pat. No. 4,312,801. The solvent can be present in an amount of from about 20 to about 99 wt. % of the catalyst composition.

In one embodiment, a composition in accordance with the present invention comprises: 100 pt. wt. polymer component (A); about 0.1 to about 10 pt. wt. crosslinker component (B); about 0.01 to about 7 pt. wt. catalyst component (C); about 0.1 to about 5, in one embodiment 0.15-1 pt. wt., of an adhesion promoter component (D); about 0 to about 300 pt. wt. filler component (E); about 0.01 to about 7 pt. wt. of acidic compound (F); optionally 0 to about 15 pt. wt. component (G), where the pt. wt. of components (B)-(G) are each based on 100 parts of the polymer component (A). In one embodiment the composition comprises the component (F) in an amount of from about 0.01 to about 1 pt. wt. per 100 pt. wt. of component (A). In still another embodiment, the composition comprises the catalyst (C) in an amount of from about 0.1 to about 0.8 wt. pt. per 100 wt. pt of component (A).

In one embodiment, the composition comprises: 100 pt. wt of component (A); 0.5 to about 3 pt. wt of at least one alkoxysilane as crosslinker (B); 0.1 to about 2 pt. wt. of Fe-III-3-methyl-penta-2,4-dionate as catalyst (C); 0.1 to about 1.5 pt. wt. of Bis(3-propyltrimethoxysilyl)amine as adhesion promoter (D); 0 to about 300 pt. wt of component (E); 0.01 to about 0.5 pt. wt. of Versatic Acid™ 10 as component (F); whereby this composition can be stored in the absence of humidity and is curable in the presence of humidity upon exposure to ambient air.

In another embodiment, the composition comprises: 100 pt. wt of component (A); 0.5 to about 3 pt. wt of at least one alkoxysilane as crosslinker (B); 0.1 to about 2 pt. wt. of Bi-III-(octoate) as catalyst (C); 0.1 to about 1.5 pt. wt. of bis(3-propyltrimethoxysilyl)amine as adhesion promoter (D); 0 to about 300 pt. wt of component (E); 0.01 to about 0.5 pt. wt. of Versatic Acid™ 10 as component (F); whereby this composition can be stored in the absence of humidity and is curable in the presence of humidity upon exposure to ambient air.

It will be appreciated that the curable compositions may be provided as either a One-Part composition or a two-part composition. A One-Part composition refers to a composition comprising a mixture of the various components described above. A two-part composition may comprise a first portion and a second portion that are separately stored and subsequently mixed together just prior to application for curing. In one embodiment, a two-part composition comprises a first portion (P1) comprising a polymer component (A) and a crosslinker component (B), and a second portion (P2) comprising the catalyst component (C) comprising the Fe(III) or Bi(III) complex. The first and second portions may include other components (F) and/or (G) as may be desired for a particular purpose or intended use. For example, in one embodiment, the first portion (P1) may optionally comprise an adhesion promoter (D) and/or a filler (E), and the second portion (P2) may optionally comprise auxiliary substances (G), a cure rate modifying component (F), and water (G).

In one embodiment, a two-part composition comprises (i) a first portion comprising the polymer component (A), optionally the filler component (E), and optionally the acidic compound (F); and (ii) a second portion comprising the crosslinker (B), the catalyst component (C), the adhesive promoter (D), and the acidic compound (F), where portions (i) and (ii) are stored separately until applied for curing by mixing of the components (i) and (ii).

An exemplary "Two-Part" composition comprises: a first portion (i) comprising 100 pt. wt of component (A), and 0 to 70 pt. wt of component (E); and a second portion (ii) comprising 0.1 to 5 pt. wt of at least one crosslinker (B); 0.01 to 2 pt. wt. of a catalyst (C); 0.1 to 2 p. wt. of an adhesion promoter (D); and 0.02 to 1 pt. wt. component (F).

The curable compositions may be used in a wide range of applications including as materials for sealing, mold making, adhesives, coatings in sanitary rooms, glazing, prototyping, joint seal between different materials, e.g., sealants between ceramic or mineral surfaces and thermoplastics, paper release, impregnation, and the like. A curable composition in accordance with the present invention comprising a Fe(III) or Bi(III) complex as a catalyst may be suitable for a wide variety of applications such as, for example, a general purpose and industrial sealant, potting compound, caulk, adhesive or coating for construction use, insulated glass (IG), structural glazing (SSG), where glass sheets are fixed and sealed in metal frame; caulks, adhesives for metal plates, car bodies, vehicles, electronic devices and the like. Furthermore, the present composition may be used either as a one-part RTV-1K or as a two-part room temperature vulcanizing (RTV-2K) formulation which can adhere onto broad variety of metal, mineral, ceramic, rubber or plastic surfaces.

Curable compositions comprising Fe(III) or Bi(III) catalyst compounds may be further understood with reference to the following Examples.

Examples

Procedure for making 3-methyl-penta-2,4-dionate-iron (III)

To a solution of iron (III) chloride hexahydrate (20 g) (74 mmol) dissolved in distilled water (155.0 ml) taken in a round-bottom flask, 3-methyl acetylacetone (40 g) (351 mmol) in methanol (80 ml) was added over a period of 15 min, with stirring. To the resultant mixture, a solution of sodium acetate (28.6 g) (349 mmol) dissolved in distilled water (70 ml) was added. The mixture was left stirring at room temperature and maintained at this temperature for 15 min. The solid product (Fe(III)MAA) was isolated by filtration. The FeMAA further thoroughly air-dried prior to storing in sealed sample tubes. Formation of FeMAA complex is confirmed using FTIR, SEM-EDS and elemental analysis techniques.

General Experimental Procedure for "One-Part"-Composition with a Fe Catalyst

To a mixture of 10 g of ethyl polysilicate (EPS), 0 or 0.2 g carboxylic acids 5 g adhesion promoter was taken in plastic cup and mixed with 528 g of SiOH-terminated polydimethylsiloxane having a viscosity of 25 Pa·s (25° C.), 200 g of SiOH-terminated polydimethylsiloxane having a viscosity of 3.6 Pa·s (25° C.) followed by the addition of 264 g of a silane treated silica filler (Aerosil R972) mixing this compound by using a Hauschild mixer for 1.5 min. After this step, 1 or 3 g of the catalyst tin or iron catalysts are added and dispersed. The mixed formulation was a) poured into a Teflon mold (length×breadth×depth ~10 cm×10 cm×1 cm) placed inside a fume hood. The surface curing (TFT) and bulk curing was monitored as a function of time (maximum of 7 days). A second portion b) was submitted to an ageing test simulating the storage stability.

Measurement of Surface Curing (TFT) and Bulk Curing

The surface cure was denoted by tack free time (TFT). In a typical TFT measurement, a stainless steel (SS) weight (weighing ~10 g) was placed on the surface of the formulation spread on the Teflon mold to infer the tackiness of the surface, as whether any material is adhered to the surface of the SS weight or not. TFT is defined as the time taken for getting a non-tacky surface. Bulk curing is the time taken for complete curing of formulation throughout the thickness (i.e. Top to bottom) and it is monitored as a function of time (visual inspection).

Measurement of the Storage Stability

For simulating the storage stability in a closed cartridge over several months the aforementioned "One-Part"-composition was submitted to an aging test. Hereby each of the closed cartridges comprising a single composition were kept in an oven for (1) 4 hours at 50° C., or (2) 5 days at 70° C., after which specified period the mixture is removed from oven and allow it to attain room temperature (25° C.). Then the mixtures were discharged by extrusion into a Teflon mold (length×breadth×depth ~10 cm×10 cm×1 cm) placed inside a fume hood in order to start the cure by interaction of ambient air having about 50% humidity at 25° C. The surface curing (TFT) and bulk curing was monitored as a function of time (maximum of 7 days) and Shore A hardness in order to determine to what extent the compositions maintained performance after storage under accelerated conditions. The increased temperature for the storage test should simulate the storage effect at room temperature (25° C. 50% relative humidity) over longer times in a kind of time lapse.

Table 1 illustrates the performance of the Fe(III) catalysts and its ligands as compared to the tin catalysts and compared to compositions that do not employ an adhesion promoter (D) or a cure accelerator (F).

TABLE 1

|  |  | C1 | C2 | C3 | Ex. 1 | Ex. 2 | Ex. 3 | Ex. 4 | Ex. 5 | Ex. 6 | Ex. 7 |
|---|---|---|---|---|---|---|---|---|---|---|---|
| SiOH term. Linear PDMS 25 Pa·s |  | 52.8 | 52.8 | 52.8 | 52.8 | 52.8 | 52.8 | 52.8 | 52.8 | 52.8 | 52.8 |
| SiOH term. Linear PDMS 3.6 Pa·s |  | 20 | 20 | 20 | 20 | 20 | 20 | 20 | 20 | 20 | 20 |
| Treated fumed silica R972 |  | 26.4 | 26.4 | 26.4 | 26.4 | 26.4 | 26.4 | 26.4 | 26.4 | 26.4 | 26.4 |
| Ethyl polysilicate |  | 1 | 1 | 1 | 1 | 1 | 1 | 1 | 1 | 1 | 1 |
| Bis(3-propyltrimethoxysilyl)amine |  | 0.5 | 0.5 | 0.5 | 0.5 | 0.5 | 0.5 | 0.5 | 0.5 | 0.5 | 0.5 |
| Dibuytltindilaurate |  | 0.1 | 0.1 |  |  |  |  |  |  |  |  |
| Iron (III) penta-2,4-dionate |  |  |  | 0.3 | 0.3 | 0.3 | — |  |  |  |  |
| 3-methyl-penta-2,4-dionate-Iron (III) |  |  | — | — |  |  | 0.3 | 0.3 | 0.3 | 0.3 | 0.05 |
| Lauric acid |  |  |  |  | 0.02 |  |  | 0.02 |  |  |  |
| Steric acid |  |  |  |  |  | 0.02 |  |  | 0.02 |  |  |
| Versatic acid |  |  | 0.02 |  |  |  |  |  |  | 0.02 | 0.02 |
| TFT (initial) | [min] | 13 | 11 | 80 | 46 | 67 | 50 | 52 | 49 | 35 | 16 |
| TFT (after 4 h @ 50° C.) | [min] | 15 | 13 | 240 | 61 | 68 | 43 | 40 | 44 | 31 | 18 |
| TFT (after 5 days @ 70° C.) | [min] | 17 | 15 | 240 | 102 | 185 | 40 | 35 | 35 | 30 | 20 |
| Bulk cure (initial) | [h] | 6 | 6 | 10 | 18 | 18 | 8 | 8 | 8 | 8 | 5 |
| Bulk cure (after 4 h @ 50° C.) | [h] | 6 | 6 | >24 | 18 | 18 | 8 | 8 | 8 | 8 | 5 |
| Bulk cure (after 5 days @ 70° C.) | [h] | 6 | 6 | >24 | 18 | 18 | 8 | 8 | 8 | 8 | 5 |
| Hardness-(initial) (up/down)* | ° Shore A | 58/60 | 50/55 | 48/48 | 52/52 | 51/52 | 50/52 | 58/60 | 58/60 | 59/60 | 59/61 |
| Hardness-(after 4 h @ 50° C.)* | ° Shore A | 58/60 | 50/48 | 48/49 | 51/53 | 51/53 | 55/55 | 58/60 | 58/60 | 58/60 | 58/60 |
| Hardness-(after 5 days @ 70° C.)* | ° Shore A | 55/56 | 50/50 | 48/50 | 46/44 | 50/50 | 55/54 | 58/60 | 58/60 | 58/60 | 58/60 |
| Adhesion to PVC |  | x | x | NA | NA | NA | x | x | x | x | x |
| Adhesion to glass |  | x | x | NA | NA | NA | + | + | + | + | + |
| Adhesion to polycarbonate |  | x | x | NA | NA | NA | x | + | + | + | + |
| Adhesion to Al |  | x | x | NA | NA | NA | + | + | + | + | + |

)*hardness measured on top and bottom of the molded sheet (./.)

x - No adhesion; + - Good adhesion

Comments upon C1-C3, Examples 1-7:

The comparative examples C1-C3 and the examples 1-7 show the effect of a catalyst replacement. If the tin catalyst is replaced by the iron acetylacetonate shown in comparative example C3 the Tack-Free-Time and Bulk Cure Time are enlarged. If the iron (III) (3-methyl-penta-2,4-dionate) is used as shown in the example 3 the Tack-Free-Time and Bulk Cure Time are shorter than in comparative example C1 but the curing times don't yet have the level the composition with DBTDL in comparison example C1. In addition the level of hardness is slightly lower in example 3 than C1. The addition of the carboxylic acids in table 1 has divergent effects in the case of the tin and iron catalysts. C2 shows slightly decreased curing times but a lower hardness than C1. In the case of the iron catalysts, the carboxylic acids decrease the Tack-Free-Time and Bulk Cure Time, again as shown by example 1, 2, 4, 5, 6 and 7, and increase the hardness, whereby the Versatic Acid in example 6 and 7 provides the shortest curing times and highest level of hardness when used together with Fe(III)-3-methyl-penta-2,4-dionate. In addition, looking at, example 7, it was observed that the inventive composition can be cured with very low catalyst concentration without negative effects on cure times.

Bi Catalyst—General Experimental Procedure for "Two-Part" Composition

To a mixture of 10 g of ethyl polysilicate (EPS), were added 0.3 g carboxylic acids of table 2.5 g adhesion promoter, and catalyst (4 g) used as P2, 996.6 g of silanol-stopped polydimethylsiloxane having a viscosity of 600 mPa·s (25° C.) Mw=22000 g/mol containing a silica filler used as P1 was added and mixed using a Hauschild mixer for 1.5 min. The mixed formulation was poured into a Teflon mold (length×breadth×depth ~10 cm×10 cm×1 cm) placed inside a fume hood. The surface curing (TFT) and bulk curing was monitored as a function of time (maximum of 7 days).

Measurement of Surface Curing (TFT) and Bulk Curing

The surface cure was denoted by tack free time (TFT). In a typical TFT measurement, a stainless steel (SS) weight (weighing ~10 g) was placed on the surface of the formulation spread on the Teflon mold to infer the tackiness of the surface as whether any material is adhered to the surface of the SS weight or not. TFT is defined as the time taken for getting a non-tacky surface. Bulk curing is the time taken for complete curing of formulation throughout the thickness (i.e. Top to bottom) and it is monitored as a function of time (visual inspection).

Measurement of the Storage Stability:

For aging studies the pre-mixed mixture P2 containing ethyl polysilicate (EPS) component (B), adhesion promoter (D), catalyst (C), and cure accelerator or storage stabilizer (F) were kept in an oven for (1) 4 hours at 50° C., or (2) 5 days at 70° C., after which specified period the mixture is removed from oven and allow it to attain RT. Further this mixture is mixed the polymer-filler composition P1 comprising (A)+(B) as described before using Hauschild mixer for 1.5 min. The complete reactive formulation was poured into a Teflon mold (length×breadth×depth ~10 cm×10 cm×1 cm) placed inside a fume hood. The surface curing (TFT) and bulk curing was monitored as a function of time (maximum of 7 days) and ° Shore A hardness in order to determine, to what extent the compositions maintained performance after storage under accelerated conditions. The increased temperature for the storage test should simulate the storage effect at room temperature (25° C. 50% relative humidity) over longer times in a kind of time lapse. Table 2 compares the properties of compositions using a Bi(III) based catalyst with a carboxylate ligand to compositions using a tin based catalyst.

TABLE 2

| Formulations | C4 | C5 | C6 | C7 | C8 | C9 | Ex. 8 | Ex. 9 | Ex. 10 | Ex. 11 | Ex. 12 | Ex. 13 | Ex. 14 |
|---|---|---|---|---|---|---|---|---|---|---|---|---|---|
| Component P1 | | | | | | | | | | | | | |
| SiOH-end capped 0.6 Pa · s | 66.33 | 66.33 | 66.33 | 66.33 | 66.33 | 66.33 | 66.33 | 66.33 | 66.33 | 66.33 | 66.33 | 66.33 | 66.33 |
| Diatomite silica | 33.33 | 33.33 | 33.33 | 33.33 | 33.33 | 33.33 | 33.33 | 33.33 | 33.33 | 33.33 | 33.33 | 33.33 | 33.33 |
| Component P2 | | | | | | | | | | | | | |
| Ethyl polysilicate | 1 | 1 | 1 | 1 | 1 | 1 | 1 | 1 | 1 | 1 | 1 | 1 | 1 |
| Dibutyltin dilaurate | 0.1 | 0.1 | 0.4 | 0.4 | | | | | | | | | |
| Bismuth(2-ethylhexanoate)$_3$ | | | | | 0.4 | 0.4 | 0.3 | 0.4 | 0.4 | 0.4 | 0.3 | 0.3 | 0.3 |
| Versatic acid 10 | | 0.03 | | 0.03 | | | 0.04 | 0.03 | | | 0.04 | 0.04 | 0.04 |
| Lauric acid | | | | | | | | | 0.03 | | | | |
| Steric acid | | | | | | | | | | 0.03 | | | |
| Bis(3-propyltrimethoxysilyl)amine | 0.5 | 0.5 | | 0.5 | | 0.5 | | 0.5 | 0.5 | 0.5 | 0.25 | 0.375 | 0.125 |
| 3-Aminopropyltrimethoxy silane | | | | | | 0.5 | | | | | 0.25 | 0.125 | 0.375 |
| Properties | | | | | | | | | | | | | |
| Tack-free time immediately after mixing comp-P1 and P2 [min] | 13 | 11 | 7 | 6 | 48 hours | 15 | 18 | 8 | 19 | 17 | 10 | 10 | 13 |
| Bulk cure time - immediately after mixing comp-P1 and P2 - [h] | 6 | 6 | 5 | 5 | not cured | 5 | 7 | 5 | 7 | 7 | 5 | 5 | 5 |
| Hardness )* -immediately after mixing comp- P1 and P2 - ° Shore A | 58/60 | 50/55 | 56/58 | 58/60 | not cured | 58/59 | 42/42 | 58/60 | 56/59 | 58/60 | 48/50 | 50/50 | 42/43 |
| Tack-free time - after ageing at 70° C. for 5 days - [min] | 17 | 15 | 20 | 240 | not cured | 25 | 15 | 14 | 22 | 26 | 15 | 15 | 17 |
| Bulk cure time - after ageing at 70° C. for 5 days - [h] | 6 | 6 | 7 | 24 | not cured | 8 | 7 | 5 | 5 | 5 | 6 | 6 | 7 |
| Hardness )*-- after ageing at 70° C. for 5 days - ° Shore A | 52/50 | 50/48 | 50/52 | 52/58 | not cured | 58/58 | | 60/65 | 56/58 | 56/58 | N/A | N/A | N/A |
| Adhesion to Glass-I* | x | x | x | x | N/A | x | N/A | o | o | o | o | o | o |
| Adhesion to Glass II* | o | o | o | o | N/A | o | o | o | o | o | o | o | o |
| Adhesion to Aluminum I* | x | x | x | x | N/A | x | N/A | x | x | x | o | o | o |
| Adhesion to Aluminum II* | o | o | o | o | N/A | o | o | o | o | o | o | o | o |
| Adhesion to Polycarbonate | x | x | x | x | N/A | x | x | x | x | x | o | o | o |
| Adhesion to Polyvinyl chloride | x | x | x | x | N/A | x | N/A | x | x | x | N/A | N/A | N/A |
| Adhesion to Epoxy glass | o | o | o | o | N/A | o | o | o | o | o | o | o | o |
| Adhesion to Polybutylene terephthalate | x | x | x | x | N/A | x | x | x | x | x | x | o | o |
| Adhesion to Noryl ® | x | x | x | x | N/A | x | x | x | x | x | o | o | o | x - No adhesion; + - Good adhesion
)* hardness measured on top and bottom of the molded sheet (./.)

Comments Upon C4-C9, Examples 8-10:

The examples 8-11 and comparative example 9 show the effect of the replacement of the tin catalyst versus the inventive bismuth catalyst. Examples 12-14 show the effect of using a combination of adhesion promoters with the Bi catalyst. The simple replacement of the tin catalyst by the Bi-catalyst, as shown in comparative example C8, results in inferior curing properties. If, however, the Bi-catalyst is replaced and combined with the adhesion promoter (D) in comparison example C9, the Tack-Free-Time and Bulk Cure Time are decreased but the adhesion properties on glass is still weak.

The further addition of the carboxylic acids of table 2 improves the adhesion properties on glass in all cases of examples 8-11 but only the addition of Versatic Acid™ 10 does decrease in the same time the Tack-Free-Time and Bulk Cure Time again. The effect of carboxylic acids could not be concluded from its interaction with the tin catalyst, since the Versatic Acid works different on the adhesion properties as shown in comparative example C5 and C7 of table 2.

The addition of the carboxylic acids in table 2 has divergent effects in case of tin and bismuth catalysts. In the case of the tin catalyst, the addition of carboxylic acids does not improve the adhesion properties comparative example C5 and C7. The effect on hardness and curing times in C5 and C7 is not uniform, whereby example 8 provides an optimum of short curing time and adhesion properties.

Embodiments of the invention have been described above and modifications and alterations may occur to others upon the reading and understanding of this specification. The claims as follows are intended to include all modifications and alterations insofar as they come within the scope of the claims or the equivalent thereof.

We claim:

1. A composition for forming a cured polymer composition comprising:
   (A) a polymer having at least a reactive silyl group;
   (B) a crosslinker or chain extender chosen from an alkoxysilane, an alkoxysiloxane, an oximosilane, an oximosiloxane, an enoxysilane, an enoxysiloxane, an aminosilane, a carboxysilane, a carboxysiloxane, an alkylamidosilane, an alkylamidosiloxane, an arylamidosilane, an arylamidosiloxane, an alkoxyaminosilane, an alkaryaminosiloxane, an alkoxycarbamatosilane, an alkoxycarbamatosiloxane, and combinations of two or more thereof;
   (C) about 0.01-7 parts per weight per 100 parts per weight of the polymer (A) of a catalyst selected from a Fe(III) complex of the Formula (1), a Bi(III) complex of the Formula (2), or a combination thereof:

$$Fe^{III}Y_{3-c}A_c \qquad (1)$$

$$Bi^{III}Y_{3-c}A_c \qquad (2)$$

wherein Y is a chelating ligand chosen from a diketonate, a diamine, a triamine, an aminoacetate, a nitriloacetate, a bipyridin, a glyoxime, or a combination of two or more thereof; and A is an anion chosen from substituted, unsubstituted alkyl- and aryl carboxylates, and c is a number between 0 to 3 or an integer;

(D) at least one adhesion promoter chosen from a silane or siloxane other than the compounds listed under (B);

(E) optionally, a filler component; and (F) at least one acidic compound chosen from a phosphate ester, a phosphonate, a phosphite, a phosphine, a sulfite, a pseudohalogenide, a branched alkyl carboxylic acid, and a combination of two or more thereof.

2. The composition of claim 1, wherein the chelating agent Y comprises a substituted diketonate, the carboxylate anion A is chosen from pentanoate, hexanoate, heptanoate, octoate, neodecanoate, 2-ethylhexanoate, or a combination of two or more thereof.

3. The composition of claim 1, wherein catalyst (C) comprises a complex $Fe^{III}Y_{3-c}A_c$ whereby c=0 and Y is 3-methyl-2,4-pentadionate.

4. The composition of claim 1, wherein catalyst (C) comprises a complex $Bi^{III}Y_{3-c}A_c$ and whereby c=3 and the anion A is a branched $C_4$-$C_{19}$ alkyl carboxylate.

5. The composition of claim 1 comprising the catalyst (C) in an amount of about 0.1 to about 2 parts per weight per 100 parts per weight of the polymer (A).

6. The composition of claim 1 comprising the catalyst (C) in an amount of about 0.2 to about 0.7 parts per weight per 100 parts per weight of the polymer (A).

7. The composition of claim 1, wherein the acidic component (F) is added in a molar ratio of (F):(C) of 1:10 to 1:4.

8. The composition of claim 1, wherein the component (F) is chosen from a mono ester of a phosphate; a phosphonate of the formula $(R^3O)PO(OH)_2$, $(R^3O)P(OH)_2$, or $R^3P(O)(OH)_2$ where $R^3$ is a $C_1$-$C_{18}$-alkyl, a $C_2$-$C_{20}$-alkoxyalkyl, phenyl, a $C_7$-$C_{12}$-alkylaryl, a poly($C_2$-$C_4$-alkylene) oxide ester or its mixtures with diesters; a branched alkyl $C_4$-$C_{14}$-alkyl carboxylic acid; or a combination of two or more thereof.

9. The polymer composition of claim 1, wherein the polymer (A) has the formula (2)

$$[R^1{}_aR^2{}_{3-a}Si-Z-]_n-X-Z-SiR^1{}_aR^2{}_{3-a} \qquad (2)$$

where X is chosen from a polyurethane; a polyester; a polyether; a polycarbonate; a polyolefin; a polypropylene; a polyesterether; and a polyorganosiloxane having units of $R_3SiO_{1/2}$, $R_2SiO$, $RSiO_{3/2}$, and/or $SiO_{4/2}$, n is 0 to 100, a is 0 to 2, R and $R^1$ can be identical or different at the same Si-atom and chosen from a $C_1$-$C_{10}$-alkyl; a $C_1$-$C_{10}$ alkyl substituted with one or more of Cl, F, N, O or S; a phenyl; a $C_7$-$C_{16}$ alkylaryl; a $C_7$-$C_{16}$ arylalkyl; a $C_2$-$C_4$ polyalkylene ether; or a combination of two or more thereof, $R^2$ is chosen from OH, a $C_1$-$C_8$-alkoxy, a $C_2$-$C_{18}$-alkoxyalkyl, an oximoalkyl, an enoxyalkyl, an aminoalkyl, a carboxyalkyl, an amidoalkyl, an amidoaryl, a carbamatoalkyl, or a combination of two or more thereof, and is a bond, a divalent unit selected from the group of a $C_1$-$C_8$ alkylene, or O.

10. The composition of claim 1, wherein the crosslinker component (B) is chosen from tetraethylorthosilicate (TEOS), a polycondensate of TEOS; methyltrimethoxysilane (MTMS); vinyl-trimethoxysilane; methylvinyldimethoxysilane; dimethyldiethoxysilane; vinyltriethoxysilane; tetra-n-propylorthosilicate; vinyltris(methylethylketoxime)silane; methyltris(methylethylketoxime)silane; trisacetamidomethylsilane; bisacetamidodimethylsilane; tris(N-methyl-acetamido)methylsilane; bis(N-methylacetamido)dimethylsilane; (N-methyl-acetamido)methyldialkoxysilane; trisbenzamidomethylsilane; trispropenoxymethylsilane; alkyldialkoxyamidosilanes; alkylalkoxybisamidosilanes; $CH_3Si(OC_2H_5)_{1-2}(NHCOR)_{2-1}$; $(CH_3Si(OC_2H_5)(NCH_3COC_6H_5)_2$; $CH_3Si(OC_2H_5)-(NHCOC_6H_5)_2$; methyldimethoxy(ethylmethylketoximo)silane; methylmethoxybis(ethylmethylketoximo)silane; methyldimethoxy(acetaldoximo)silane; methyldimethoxy(N-methylcarbamato)silane; ethyldimethoxy(N-methylcarbamato)silane; methyldimethoxyisopropenoxysilane; trimethoxyisopropenoxysilane; methyltri-iso-propenoxysilane; methyldimethoxy(but-2-ene-2-oxy)silane; methyldimethoxy(1-phenylethenoxy)silane; methyldimethoxy-2(1-carboethoxypropenoxy)silane; methylmethoxydi-N-methylaminosilane; vinyldimethoxymethylaminosilane; tetra-N,N-diethylaminosilane; methyldimethoxymethylaminosilane; methyltricyclohexylaminosilane; methyldimethoxyethylaminosilane; dimethyldi-N,N-dimethylaminosilane; methyldimethoxyisopropylaminosilane; dimethyldi-N,N-diethylaminosilane; ethyldimethoxy(N-ethylpropionamido)silane; methyldimethoxy(N-methylacetamido)silane; methyltris(N-methylacetamido)silane; ethyldimethoxy(N-methylacetamido)silane; methyltris(N-methylbenzamido)silane; methylmethoxybis(N-methylacetamido)silane; methyldimethoxy(caprolactamo)silane; trimethoxy(N-methylacetamido)silane; methyldimethoxyethylacetimidatosilane; methyldimethoxypropylacetimidatosilane; methyldimethoxy(N,N',N'-trimethylureido)silane; methyldimethoxy(N-allyl-N',N'-dimethylureido)silane; methyldimethoxy(N-phenyl-N',N'-dimethylureido)silane; methyldimethoxyisocyanatosilane; dimethoxydiisocyanatosilane; methyldimethoxythioisocyanatosilane; methylmethoxydithioisocyanatosilane, or a combination of two or more thereof.

11. The composition of claim 1, wherein the adhesion promoter component (D) is chosen from an aminoalkyltrialkoxysilane, an aminoalkylalkyldialkoxysilane, a bis(alkyltrialkoxysilyl)amine, a tris(alkyltrialkoxysilyl)amine, a tris(alkyltrialkoxysilyl)cyanuarate, and a tris(alkyltrialkoxysilyl)isocyanuarate, or a combination of two or more thereof.

12. The composition of claim 1 comprising about 0.1 to about 5 pt. wt. of the adhesion promoter (D) per 100 parts per weight of the polymer (A).

13. The composition of claim 1, wherein the adhesion promoter component (D) is chosen from an aminoalkyltrialkoxysilane, an aminoalkylalkyldialkoxysilane, a bis(alkyltrialkoxysilyl)amine, a tris(alkyltrialkoxysilyl)amine, a tris(alkyltrialkoxysilyl)cyanuarate, and a tris(alkyltrialkoxysilyl)isocyanuarate, or a combination of two or more thereof.

14. The composition of claim 1 wherein the adhesion promoter comprises an aminoalkyltrialkoxysilane and a bis(alkyltrialkoxysilyl)amine.

15. The composition of claim 1, wherein the adhesion promoter comprises bis(3-propyltrimethoxysilyl)amine and 3-aminopropyltrimethoxy silane.

16. The polymer composition of claim 1 wherein the polymer component (A) has the formula (4):

$$R^2{}_{3-a}R^1{}_aSi-Z-[R_2SiO]_x[R^1{}_2SiO]_y-Z-SiR^1{}_aR^2{}_{3-a} \qquad (4)$$

whereby
x is 0 to 10000;
y is 0 to 1000;
a is 0 to 2;
R is methyl;
$R^1$ is chosen from a $C_1$-$C_{10}$-alkyl; a $C_1$-$C_{10}$ alkyl substituted with one or more of Cl, F, N, O or S; a phenyl; a $C_7$-$C_{16}$ alkylaryl; a $C_7$-$C_{16}$ arylalkyl; a $C_2$-$C_4$ polyalkylene ether; or a combination of two or more thereof, and other siloxane units may be present in amounts less than 10 mol. % preferably methyl, vinyl, phenyl;
$R^2$ is chosen from OH, a $C_1$-$C_8$-alkoxy, a $C_2$-$C_{18}$-alkoxyalkyl, an oximoalkyl, an enoxyalkyl, an aminoalkyl, a carboxyalkyl, an amidoalkyl, an amidoaryl, a carbamatoalkyl, or a combination of two or more thereof, and
Z is —O—, bond, or —$C_2H_4$—.

17. The composition of claim 1, further comprising a solvent chosen from an alkylbenzene, a trialkyphosphate, a triarylphosphate, a phthalic acid ester, an arylsulfonic acid ester having a viscosity-density constant (VDC) of at least 0.86 that is miscible with a polyorganosiloxanes and catalyst component (C), a polyorganosiloxane devoid of reactive groups and having a viscosity of less than 2000 mPa·s at 25° C., or a combination of two or more thereof.

18. The composition of claim 1 comprising:
100 pt. wt of component (A),
0.1 to about 10 pt. wt of at least one crosslinker (B),
0.01 to about 7 pt. wt. of a catalyst (C),
0.1 to about 5 pt. wt. of an adhesion promoter (D),
0 to about 300 pt. wt of component (E),
0.01 to about 8 pt. wt. of component (F),
whereby this composition can be stored in the absence of humidity and is curable in the presence of humidity upon exposure to ambient air.

19. The composition of any claim 1 comprising:
100 pt. wt of component (A),
0.5 to about 3 pt. wt of at least one alkoxysilane as crosslinker (B),
0.1 to about 2 pt. wt. of Fe-III-3-methyl-penta-2,4-dionate as catalyst (C),
0.1 to about 1.5 pt. wt. of bis(3-propyltrimethoxysilyl) amine as adhesion promoter (D),
0 to about 300 pt. wt of component (E),
0.01 to about 0.5 pt. wt. of Versatic Acid™ 10 as component (F),
whereby this composition can be stored in the absence of humidity and is curable in the presence of humidity upon exposure to ambient air.

20. The composition of claim 1 comprising:
100 pt. wt of component (A),
0.5 to about 3 pt. wt of at least one alkoxysilane as crosslinker (B),
0.1 to about 2 pt. wt. of Bi-III-(octoate) as catalyst (C),
0.1 to about 1.5 pt. wt. of Bis(3-propyltrimethoxysilyl) amine as adhesion promoter (D),
0 to about 300 pt. wt of component (E),
0.01 to about 0.5 pt. wt. of Versatic Acid™ 10 as component (F),
whereby this composition can be stored in the absence of humidity and is curable in the presence of humidity upon exposure to ambient air.

21. The composition of claim 1 wherein the adhesion promoter comprises an aminoalkyltrialkoxysilane and a bis(alkyltrialkoxysilyl)amine.

22. The composition of claim 21 comprising about 0.1 to about 5 pt. wt. of the adhesion promoter (D) per 100 parts per weight of the polymer (A).

23. The composition of any claim 21 comprising about 0.14 to about 2 pt. wt. of the adhesion promoter (D) per 100 parts per weight of the polymer (A).

24. The composition of claim 1, wherein the adhesion promoter comprises bis(3-propyltrimethoxysilyl)amine and 3-aminopropyltrimethoxy silane.

25. The composition of claim 24 comprising about 0.1 to about 5 pt. wt. of the adhesion promoter (D) per 100 parts per weight of the polymer (A).

26. The composition of any claim 24 comprising about 0.14 to about 2 pt. wt. of the adhesion promoter (D) per 100 parts per weight of the polymer (A).

27. A cured polymer formed from the composition of claim 1.

28. The cured polymer of claim 27 in the form of an elastomeric, seal, duromeric seal, an adhesive, a coating, an encapsulant, a shaped article, a mold, or an impression material.

* * * * *